United States Patent
Kao et al.

(10) Patent No.: US 11,793,858 B2
(45) Date of Patent: *Oct. 24, 2023

(54) BACTERICIDAL PEPTIDES AND USES THEREOF

(71) Applicant: INDIANA UNIVERSITY RESEARCH AND TECHNOLOGY CORPORATION, Indianapolis, IN (US)

(72) Inventors: C. Cheng Kao, Bloomington, IN (US); Antonio Cembellin Prieto, Bloomington, IN (US); Dean Rowe-Magnus, Bloomington, IN (US)

(73) Assignee: INDIANA UNIVERSITY RESEARCH AND TECHNOLOGY CORPORATION, Indianapolis, IN (US)

(*) Notice: Subject to any disclaimer, the term of this patent is extended or adjusted under 35 U.S.C. 154(b) by 88 days.

This patent is subject to a terminal disclaimer.

(21) Appl. No.: 17/045,614

(22) PCT Filed: Apr. 15, 2019

(86) PCT No.: PCT/US2019/027454
§ 371 (c)(1),
(2) Date: Oct. 6, 2020

(87) PCT Pub. No.: WO2019/200378
PCT Pub. Date: Oct. 17, 2019

(65) Prior Publication Data
US 2021/0154266 A1    May 27, 2021

Related U.S. Application Data

(63) Continuation of application No. 16/146,165, filed on Sep. 28, 2018, now Pat. No. 10,624,947.

(60) Provisional application No. 62/741,288, filed on Oct. 4, 2018, provisional application No. 62/657,222, filed on Apr. 13, 2018.

(51) Int. Cl.
*A61K 38/17* (2006.01)
*A61P 31/04* (2006.01)

(52) U.S. Cl.
CPC .............. *A61K 38/17* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 10,138,282 B2 | 11/2018 | Kao et al. | |
| 10,624,947 B2 | 4/2020 | Kao et al. | |
| 2004/0170642 A1 | 9/2004 | Fritz et al. | |
| 2005/0058689 A1 | 3/2005 | McDaniel | |
| 2010/0239611 A1 | 9/2010 | Van Drunen Littel et al. | |
| 2010/0316643 A1 | 12/2010 | Eckert et al. | |
| 2011/0250626 A1 | 10/2011 | Williams et al. | |
| 2013/0252880 A1* | 9/2013 | Kallenbach | A61P 31/10 514/3.3 |
| 2014/0296137 A1 | 10/2014 | Rajamani et al. | |

FOREIGN PATENT DOCUMENTS

| | | | |
|---|---|---|---|
| WO | 2010/043039 | | 4/2010 |
| WO | WO2010043039 | * | 4/2010 |
| WO | 2017172929 A1 | | 10/2017 |

OTHER PUBLICATIONS

LifeTein (https://www.lifetein.com/Peptide-Synthesis-Amidation-Acetylation.html ;Aug. 7, 2014).*
UniProt sequence P54228 (CTHL6_BOVIN)(<https://www.uniprot.org/uniprot/P54228>Oct. 1, 1996).*
GenBank sequence AKA21233.1 (<https://www.ncbi.nlm.nih.gov/protein/aka21233>) submitted May 10, 2014).*
PCT International Search Report and Written Opinion completed by the ISA/US dated Aug. 5, 2019 and issued in connection with PCT/US2019/027454.
LIFETEIN. Free Modifications: N-terminal Acetylation and C-terminal Amidation. (online) Oct. 19, 2016 (retrieved Aug. 5, 2019]. Available on the internet: <URL: https://web.archive.org/web/20161019191935/http://www.lifetein.com/Peptide-Synthesis-Amidation-Acetylation.html>.
Acosta-Smith et al. Bovine Lactoferrin and Lactoferrin-Derived Peptides Inhibit the Growth of Vibrio choleras and Other Vibrio species. Front Microbiol Jan. 11, 2018 vol. 8 No. 2633 pp. 1-14.
International Search Report and Written Opinion of PCT/US17/24766, dated Sep. 5, 2017.
Zasloff, M., "Defending the epithelium," Nature Medicine, vol. 12, No. 6, Jun. 2006, 607-8.
Zanetti, M., "Cathelicidins, multifunctional peptides of the innate immunity," Journal of Leukocyte Biology, vol. 75, Jan. 2004, 39-48.
Wright, A.C., et al. "Role of iron in the pathogenesis of Vibrio vulnificus infection," Infection and Immunity, 1981, vol. 34, No. 2, 503-7.
Wang, G. "Structures of Human Host Defense Cathelicidin LL-37 and its smallest antimicrobial Peptide KR-12 in lipid micelles," The Journal of Biological Chemistry, 2008, vol. 283, No. 47, 32637-43.
Starks, A.M., et al. "Pathogenesis of infection by clinical and environmental strains of Vibrio vulnificus in iron-dextran-treated mice," Infection and Immunity, 2000, vol. 68, 5785-93.

(Continued)

*Primary Examiner* — Julie Ha
*Assistant Examiner* — Tara L Martinez
(74) *Attorney, Agent, or Firm* — Barnes & Thornburg LLP

(57) ABSTRACT

Antimicrobial compositions having bactericidal activity are described. Also described is a method of treating bacterial infections using compositions comprising antimicrobial peptides or variants thereof.

11 Claims, 7 Drawing Sheets

Figure 1:
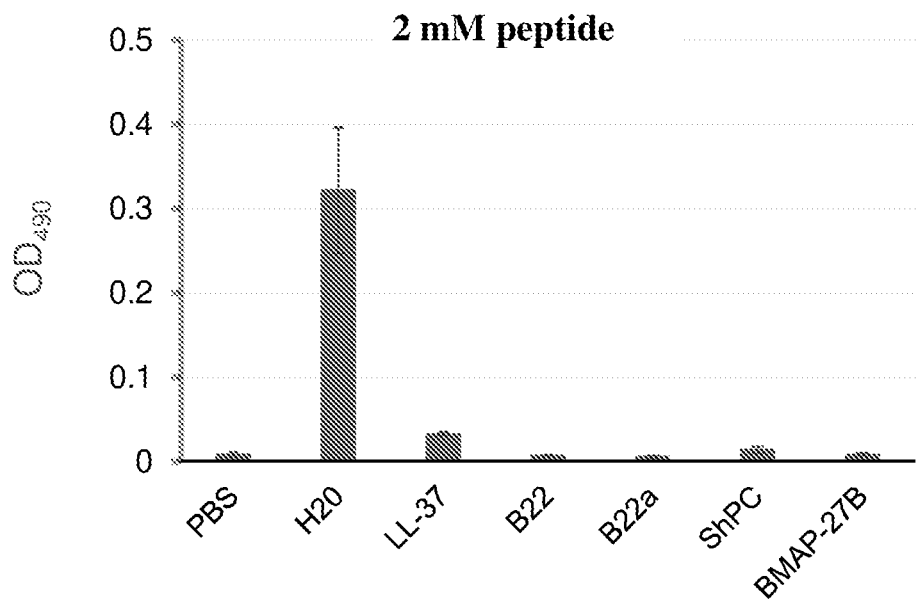

Specification includes a Sequence Listing.

(56) References Cited

OTHER PUBLICATIONS

Sanchez, G.V., et al. "Klebsiella pneumoniae antimicrobial drug resistance, United States," Emerging Infectious Disease, 2013, vol. 19, No. 1, 133-6.

Rhouma, M. et al. "Colistin in pig production: chemistry, mechanism of antibacterial action, microbial resistance, and one health perspectives, "Frontiers in Microbiology, 2016, vol. 7, Article 1789, 22 pages.

Nguyen, L.T., et al. "The expanding scope of antimicrobial peptide structures and their modes of action," Trends in Biotechnology, 2011, vol. 29, No. 9, 464-72.

Mediavilla, J.R., et al. "Colistin and carbapenem-resistance *Escherichia coli* harboring mcr-1 and bla NDM-5 causing a complicated urinary tract infection in a patient in the United States," American Society for Microbiology, 2016, vol. 7, Issue 4, 4 pages.

Clinical and Laboratory Standards Institute. 2015. Performance standards for antimicrobial susceptibility testing, 24th informational supplement. CLSI document M100-S25. Clinical and Laboratory Standards Institute, Wayne, PA. vol. 35, No. 3, 3 pages.

Liu, Y.Y., et al. "Emergence of plasmid-mediated colistin resistance mechanism MCR-1 in animals and human beings in China: a microbiological and molecular biological study," www.thelancet.com/infection vol. 16, Feb. 2016, 161-8.

Li, H. et al. "In vitor susceptibility of characterized b-lactamase-producing strains tested with Avibactam combinations," Antimicrobial Agents and Chemotherapy, Mar. 2015, vol. 59, No. 3, 1789-93.

Kao et al., "Cathelicidin Antimicrobial Peptides with Reduced Activation of Toll-Like Receptor Signaling Have Potent Bactericidal Activity against Colistin-Resistant Bacteria," Antimicrobial Peptides, Sep./Oct. 2016, vol. 7, Issue 5, 1-5.

Hoiby, N. et al. "Antibiotic resistance of bacterial biofilms," International Journal of Antimicrobial Agents, vol. 35, 32637-43.

Uni Prat sequence P54228 (CTH L6_BOVI N}(<https://www.uniprot.org/uniprot/P54228>Oct. 1, 1996).

Gen Bank sequence AKA21233.1 (<https://www.ncbi.nlm.nih.gov/protein/aka21233>May 10, 2014).

Matson, J.S., et al. "Polymyxin B resistance in in El Tor Vibrio cholera requires lipid acylation catalyzed by MsbB," J. Bacteriol. 2010, 192: 2044-52.

Hall C.W., and T.-F. Mah, "Molecular mechanisms of biofilm-based antibiotic resistance and tolerance in pathogenic bacteria," FEMS Microbiol. Rev., 2017, 41: 276-301.

Stewart P.S. and Costerton, J.W. "Antibiotic resistance of bacteria," Lancet, 2001, 381: 135-8.

* cited by examiner

SEQUENCE LISTING

```
<160> NUMBER OF SEQ ID NOS: 12

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid or absent
<220> FEATURE:
<221> NAME/KEY: MOD_RES
<222> LOCATION: (2)..(2)
<223> OTHER INFORMATION: Any basic amino acid or absent
<220> FEATURE:
<221> NAME/KEY: MOD_RES
<222> LOCATION: (3)..(3)
<223> OTHER INFORMATION: Any non-polar amino acid or absent
<220> FEATURE:
<221> NAME/KEY: MOD_RES
<222> LOCATION: (4)..(4)
<223> OTHER INFORMATION: Any basic amino acid or absent
<220> FEATURE:
<221> NAME/KEY: MOD_RES
<222> LOCATION: (5)..(5)
<223> OTHER INFORMATION: Any basic amino acid or absent
<220> FEATURE:
<221> NAME/KEY: MOD_RES
<222> LOCATION: (6)..(6)
<223> OTHER INFORMATION: Any non-polar amino acid
<220> FEATURE:
<221> NAME/KEY: MOD_RES
<222> LOCATION: (10)..(10)
<223> OTHER INFORMATION: Any non-polar amino acid
<220> FEATURE:
<221> NAME/KEY: MOD_RES
<222> LOCATION: (14)..(14)
<223> OTHER INFORMATION: Any non-polar amino acid
<220> FEATURE:
<221> NAME/KEY: MOD_RES
<222> LOCATION: (25)..(25)
<223> OTHER INFORMATION: Any basic amino acid or absent
<220> FEATURE:
<221> NAME/KEY: MOD_RES
<222> LOCATION: (26)..(26)
<223> OTHER INFORMATION: Any non-polar amino acid or absent
<220> FEATURE:
<221> NAME/KEY: MOD_RES
<222> LOCATION: (27)..(27)
<223> OTHER INFORMATION: Any non-polar amino acid or absent; may or may
      not be C-terminal amidation

<400> SEQUENCE: 1

Xaa Xaa Xaa Xaa Xaa Xaa Arg Lys Lys Xaa Lys Lys Leu Xaa Lys Lys
1               5                   10                  15

Leu Ser Pro Val Ile Pro Leu Leu Xaa Xaa Xaa
            20                  25

<210> SEQ ID NO 2
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid
<220> FEATURE:
<221> NAME/KEY: MOD_RES
<222> LOCATION: (5)..(5)
<223> OTHER INFORMATION: Any non-polar amino acid
<220> FEATURE:
<221> NAME/KEY: MOD_RES
<222> LOCATION: (9)..(9)
<223> OTHER INFORMATION: Any non-polar amino acid
<220> FEATURE:
<221> NAME/KEY: MOD_RES
<222> LOCATION: (20)..(20)
<223> OTHER INFORMATION: Any basic amino acid
<220> FEATURE:
<221> NAME/KEY: MOD_RES
<222> LOCATION: (21)..(21)
<223> OTHER INFORMATION: Any non-polar amino acid
<220> FEATURE:
<221> NAME/KEY: MOD_RES
<222> LOCATION: (22)..(22)
<223> OTHER INFORMATION: Any non-polar amino acid; may or may not be
      C-terminal amidation

<400> SEQUENCE: 2

Xaa Arg Lys Lys Xaa Lys Lys Leu Xaa Lys Lys Leu Ser Pro Val Ile
1               5                   10                  15

Pro Leu Leu Xaa Xaa Xaa
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe or Leu or Ala
<220> FEATURE:
<221> NAME/KEY: MOD_RES
<222> LOCATION: (5)..(5)
<223> OTHER INFORMATION: Phe or Leu
<220> FEATURE:
<221> NAME/KEY: MOD_RES
<222> LOCATION: (9)..(9)
<223> OTHER INFORMATION: Phe or Ala
<220> FEATURE:
<221> NAME/KEY: MOD_RES
<222> LOCATION: (20)..(20)
<223> OTHER INFORMATION: His or Lys
<220> FEATURE:
<221> NAME/KEY: MOD_RES
<222> LOCATION: (22)..(22)
<223> OTHER INFORMATION: may or may not be C-terminal amidation

<400> SEQUENCE: 3

Xaa Arg Lys Lys Xaa Lys Lys Leu Xaa Lys Lys Leu Ser Pro Val Ile
1               5                   10                  15

Pro Leu Leu Xaa Leu Gly
            20

<210> SEQ ID NO 4
<211> LENGTH: 22
<212> TYPE: PRT
<213> ORGANISM: Artificial Sequence
<220> FEATURE:
```

```
<223> OTHER INFORMATION: Description of Artificial Sequence:  Synthetic
      peptide
<220> FEATURE:
<221> NAME/KEY: MOD_RES
<222> LOCATION: (22)..(22)
<223> OTHER INFORMATION: C-terminal amidation

<400> SEQUENCE: 4

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence:  Synthetic
      peptide
<220> FEATURE:
<221> NAME/KEY: MOD_RES
<222> LOCATION: (22)..(22)
<220> FEATURE:
<221> NAME/KEY: MOD_RES
<222> LOCATION: (22)..(22)
<223> OTHER INFORMATION: C-terminal amidation

<400> SEQUENCE: 5

Phe Arg Lys Lys Leu Lys Lys Leu Ala Lys Lys Leu Ser Pro Val Ile
1               5                   10                  15

Pro Leu Leu Lys Leu Gly
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence:  Synthetic
      peptide
<220> FEATURE:
<221> NAME/KEY: MOD_RES
<222> LOCATION: (22)..(22)
<223> OTHER INFORMATION: C-terminal amidation

<400> SEQUENCE: 6

Ala Arg Lys Lys Leu Lys Lys Leu Ala Lys Lys Leu Ser Pro Val Ile
1               5                   10                  15

Pro Leu Leu Lys Leu Gly
            20

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid
<220> FEATURE:
<221> NAME/KEY: MOD_RES
<222> LOCATION: (5)..(5)
<223> OTHER INFORMATION: Any non-polar amino acid
<220> FEATURE:
<221> NAME/KEY: MOD_RES
<222> LOCATION: (9)..(9)
```

-continued

<223> OTHER INFORMATION: Any non-polar amino acid

<400> SEQUENCE: 7

Xaa Arg Lys Lys Xaa Lys Lys Leu Xaa Lys Lys Leu Ser Pro Val Ile
1               5                   10                  15

Pro Leu Leu

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MOD_RES
<222> LOCATION: (3)..(3)

```
<223> OTHER INFORMATION: Phe, Ala or absent
<220> FEATURE:
<221> NAME/KEY: MISC_FEATURE
<222> LOCATION: (4)..(4)
<223> OTHER INFORMATION: May or may not be present
<220> FEATURE:
<221> NAME/KEY: MISC_FEATURE
<222> LOCATION: (5)..(5)
<223> OTHER INFORMATION: May or may not be present
<220> FEATURE:
<221> NAME/KEY: MOD_RES
<222> LOCATION: (6)..(6)
<223> OTHER INFORMATION: Phe or Leu or Ala
<220> FEATURE:
<221> NAME/KEY: MOD_RES
<222> LOCATION: (10)..(10)
<223> OTHER INFORMATION: Phe or Leu
<220> FEATURE:
<221> NAME/KEY: MOD_RES
<222> LOCATION: (14)..(14)
<223> OTHER INFORMATION: Phe or Ala
<220> FEATURE:
<221> NAME/KEY: MOD_RES
<222> LOCATION: (25)..(25)
<223> OTHER INFORMATION: His, Lys or absent
<220> FEATURE:
<221> NAME/KEY: MISC_FEATURE
<222> LOCATION: (26)..(26)
<223> OTHER INFORMATION: May or may not be present
<220> FEATURE:
<221> NAME/KEY: MISC_FEATURE
<222> LOCATION: (27)..(27)
<223> OTHER INFORMATION: May or may not be present; may or may not be
      C-terminal amidation

<400> SEQUENCE: 11

Gly Arg Xaa Lys Arg Xaa Arg Lys Lys Xaa Lys Lys Leu Xaa Lys Lys
1               5                   10                  15

Leu Ser Pro Val Ile Pro Leu Leu Xaa Leu Gly
            20                  25

<210> SEQ ID NO 12
<211> LENGTH: 22
<212> TYPE: PRT
<213> ORGANISM: Artificial Sequence
<220> FEATURE:
<223> OTHER INFORMATION: Synthetic peptide

<400> SEQUENCE: 12

Phe Arg Lys Lys Leu Lys Lys Leu Phe Lys Lys Leu Ser Pro Val Ile
1               5                   10                  15

Pro Leu Leu Lys Leu Gly
            20
```

BACTERICIDAL PEPTIDES AND USES THEREOF

CROSS-REFERENCE TO RELATED APPLICATIONS

This application is a U.S. national counterpart application of international application serial No. PCT/US2019/027454 filed Apr. 15, 2019, which claims priority to U.S. Provisional Application Ser. No. 62/741,228 under 35 U.S.C. 119(e) filed on Apr. 13, 2018, to U.S. Application No. 16/146,165 filed Sep. 28, 2018, which claims priority to U.S. Provisional Application Ser. No. 62/657,222 filed Oct. 4, 2018, the disclosures of which are hereby expressly incorporated by reference in their entireties.

SEQUENCE LISTING

The instant application contains a Sequence Listing which has been submitted electronically in ASCII format and is hereby incorporated by reference in its entirety. The ASCII copy, created on Apr. 15, 2019, is named 292150seqlist_ST25.txt and is 8 kilobytes.

BACKGROUND

Bacterial infections, including foodborne illness, are a significant problem worldwide. The Center for Disease Control and Prevention (CDC) estimates that 1 in 6 Americans get sick by consuming contaminated foods or beverages. In large part, due to the use of antibiotics in the nontherapeutic growth of food animals, antibiotic-resistant bacteria that contaminate food are an increasing concern.

Enterobacteriaceae are Gram-negative bacteria that occur naturally and can cause disease. Enterobacteriaceae includes bacterial species from *Salmonella, Escherichia, Yersinia, Klebsiella,* and *Shigella.* Other disease-causing bacteria in the Enterobacteriaceae family includes *Proteus, Enterobacter, Serratia,* and *Citrobacter.* These pathogens are often referred to as enterbacteria since they are known to live in the intestines of humans and animals. For example, many members of Enterobacteriaceae are members of the gut microbial in humans and animals. Notably, *Escherichia coli* is one of the most important model organisms of Enterobacteriaceae, whose genetics and biochemistry have been well studied.

In view of the infection risks of Enterobacteriaceae bacteria, it is necessary to avoid microbial derived illness, especially among high risk people. High risk groups include people with weakened immune systems and people with chronic conditions. Therefore, proper preparation, for example sterilization, of related food products that are sensitive to Enterobacteriaceae infections is a desired development for the control of such bacteria mediated diseases.

Resistance to antimicrobial drugs is a natural phenomenon. As bacteria and other microbes are exposed to antibiotics, they will eventually develop resistance through mutations and by acquiring resistance genes from other bacteria. Therefore, continually developing new drugs and judicious use of the available drugs is required.

Antibiotic resistance can arise through the overuse, or improper use, of antibiotics in both humans and animals. For animals, there is concern for antibiotics provided to either prevent disease and/or promote growth. In half of the countries in the world, including the United States and Canada, antibiotics are still routinely used in animal feed.

Resistance that arises in animals could affect humans in two ways. First, pathogens could develop their resistance in animals before infecting people via the food supply. Second, resistance genes could be transferred from animal bacteria to human pathogens through a process known as horizontal gene transfer, where genetic material is transmitted to neighboring bacteria. In either scenario, food production safety and human health will be jeopardized by antibiotic-resistant bacteria.

Antimicrobial peptides are produced by organisms in all three domains of life on earth to decrease the establishment of other microbes. Cathelicidin are a family of antimicrobial peptides produced by metazoans. Cells such as macrophages, polymorphonuclear leukocytes (PMNs), and epithelial keratinocytes produce cathelicidins. Cathelicidins are typically of about 25-40 amino acids in length that have a high frequency of basic amino acids. Peptides of the cathelicidin family are classified as antimicrobial peptides, as they are produced in response to pathogen infection.

Cathelicidins interact with the membranes of susceptible bacteria, form higher order structures to cause ion leakage and the death of the bacteria. Cathelicidins could also bind bacterial cell wall materials, including lipopolysaccharide (LPS) molecules that are potent inducers of the inflammatory responses. In sequestering LPS, cathelicidins can suppress the inflammatory responses. These properties have made cathelicidins attractive molecules to replace antibiotics.

LL-37 is the only cathelicidin peptide produced by humans. The 37-residue LL-37 is generated by proteolytic cleavage of the C-terminal portion of the integral membrane protein, hCAP-18. As is the case with antimicrobial peptides, LL-37 has a large array of biological activities. For example, in addition to suppressing bacterial infection and suppressing the pro-inflammatory responses, LL-37 can activate the innate immune response to viral molecules, promote wound healing, and decrease fibrosis that leads to the formation of scars.

Cathelicidin peptides have been isolated from many different species of vertebrates, including but not limited to humans, monkeys, mice, rats, rabbits, guinea pigs, pandas, pigs, cattle, frogs, sheep, goats, chickens, and horses. Some species produce more than one Cathelicidins. While cathelicidins are enriched for positively-charged amino acids, the sequences and lengths for the cathelicidins produced by different animals vary.

Currently identified cathelicidins include but not limited to the following: Human: hCAP-18/LL-37; Rhesus Monkey: RL-37; Mice: CRAMP, (Cathelicidin-related Antimicrobial Peptide); Rats: rCRAMP; Rabbits: CAP-18; Guinea Pig: CAP-11; Pigs: PR-39, Prophenin, PMAP-23,36,37; Cattle: BMAP-27,28,34 (Bovine Myeloid Antimicrobial Peptides); Bac5, Bac7; Horses: eCATH-1, eCATH-2, eCATH-3; Frogs: cathelicidin-AL; Sheep: SMAP-29; and Chickens: Four cathelicidins: fowlicidins 1,2,3 and cathelicidin Beta-1.

In order to contain bacterial pathogens, there is a need to develop new and effective alternatives to kill bacteria and prevent spreading, hence prevent their potential harm to human health. This application provides one of such alternative using engineered and modified cathelicidins.

SUMMARY

This disclosure identifies compositions for effective inhibition of the growth of, or the killing of bacteria. For example, this disclosure provides compositions of antimicrobial peptides. These compositions are selected from the peptides group consisting of SEQ ID NOs: 1-11.

In some embodiments, the antimicrobial peptides of the present disclosure effectively kill and/or treat various Gram-negative bacteria, particularly members of the Enterobacteriacea family Bacterial strains of the Enterobacteriacea family comprise, of strain from the following genera: *Salmonella, Escherichia, Klebsiella, Shigella, Proteus, Enterobacter*, and *Citrobacter*. In one preferred embodiment, the aforementioned Gram-negative bacteria may comprise, consist essentially of, and/or consist of a species in the Enterobacteriaceae family, such as *Enterobacter cloacae*. In another preferred embodiment, the aforementioned Gram-negative bacteria may comprise, consist essentially of, and/or consist of an *Escherichia coli*, an *Enterobacter cloacae*, a *Klebsiella pneumoniae*, a *Pseudomonas aeruginosa*, or a mixture thereof.

In some embodiments, the antimicrobial peptides of the present disclosure may kill or treat infection by various Gram-negative bacteria. In an illustrative embodiment, antimicrobial peptides comprising an amino acid sequence of at least one of SEQ ID NOs: 4-6 or 7-9 can be used to kill or treat bacterial infection by members of the *Vibrio* genus, including *Vibrio cholera*. In some embodiments, a *Vibrio* bacterium may be killed or have its growth inhibited by contacting the bacterium with an antimicrobial peptide comprising an amino acid selected from the group consisting of SEQ ID NOs: 4-6, or a mixture thereof.

In some embodiments, an antimicrobial peptide comprises an amino acid sequence of $X_1X_2X_3X_4X_5X_6RKKX_7KKLX_8KKLSPVIPLLX_9X_{10}X_{11}$ (SEQ ID NO: 1), wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, and $X_{11}$ is a non-polar amino acid or absent; or a pharmaceutically acceptable salt thereof. In some embodiments, the antimicrobial peptide is modified with additional chemicals, such as amidates or polyethylene glycols. In some embodiments, the antimicrobial peptide is C-terminally amidated.

In one preferred embodiment, the aforementioned peptide is B22a.

In another preferred embodiment, the aforementioned peptide is B22m1.

In another preferred embodiment, the aforementioned peptide is B22m2.

In another preferred embodiment, the aforementioned peptide is C-terminally amidated.

In another preferred embodiment, the N-terminus, the C-terminus, or both the N-terminus and C-terminus are substituted.

In another preferred embodiment, the aforementioned peptide is N-terminally pegylated and C-terminally amidated.

In another preferred embodiment, the aforementioned peptide is N-terminally acylated and C-terminally pegylated.

In another preferred embodiment, the aforementioned peptide is AB22a.

In another preferred embodiment, the aforementioned peptide is AB22P.

In another preferred embodiment, the aforementioned peptide is PB22N.

This disclosure further provides a method to kill Gram-negative bacteria. The method comprises, consists essentially of, and/or consists of the steps of:

identifying a source or a subject that is infected by the Gram-negative bacteria;

providing the aforementioned source or subject with an effective amount of at least one peptide selected from the group consisting of SEQ ID NOs: 1-11; and contacting the Gram-negative bacteria with the at least one peptide selected from the group consisting of SEQ ID NOs: 1-11 or a pharmaceutically acceptable salt thereof; wherein the selected peptide kills the Gram-negative bacteria in the source or the subject.

In one preferred embodiment, the aforementioned peptide is B22a.

In another preferred embodiment, the aforementioned peptide is B22m1.

In another preferred embodiment, the aforementioned peptide is B22m2.

In another preferred embodiment, any of the aforementioned peptides are C-terminally amidated.

In another preferred embodiment, the aforementioned peptide is B22a.

In another preferred embodiment, the aforementioned peptide is B22m1.

In another preferred embodiment, the aforementioned peptide is B22m2.

In another preferred embodiment, the aforementioned peptide is C-terminally amidated.

In another preferred embodiment, the aforementioned peptide is AB22a.

In another preferred embodiment, the aforementioned peptide is AB22P.

In another preferred embodiment, the aforementioned peptide is PB22N.

This disclosure further provides a method of treating Gram-negative bacteria infected animals. The method comprises providing the infected animals effective amount of at least one peptide selected from the group consisting of SEQ ID NOs: 4-11, particularly one of SEQ ID NOs: 4-6 and/or SEQ ID NOs: 8-10. In one preferred embodiment, the aforementioned infected animals are grown from fresh water aquaculture.

In another embodiment, in accordance with the present disclosure, is a method of killing Gram-negative bacteria, the method comprises contacting Gram-negative bacteria with an antimicrobial peptide in accordance with the present disclosure; or a pharmaceutically acceptable salt thereof.

In another embodiment, in accordance with the present disclosure, is a method of treating a Gram-negative bacterial infection in a subject in need thereof, the method comprises administering to the subject an effective amount of an antimicrobial peptide according to the present disclosure; or a pharmaceutically acceptable salt thereof.

In another embodiment, a method is provided for treating a bacterial infection in a wound. The method comprises treating an infected wound by contacting the infected wound with a composition comprising an antimicrobial peptide or a pharmaceutically acceptable salt thereof.

The following numbered embodiments are contemplated and are non-limiting:

1. An antimicrobial peptide comprising an amino acid sequence of (SEQ ID NO: 1)
$X_1X_2X_3X_4X_5X_6RKKX_7KKLX_8KKLSPVIPLLX_9X_{10}X_{11}$ wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, $X_{11}$ is a non-polar amino acid or absent; and $X_{11}$ is optionally C-terminally amidated; or a pharmaceutically acceptable salt thereof.

2. The antimicrobial peptide of clause 1, wherein the antimicrobial peptide comprises an amino acid sequence of (SEQ ID NO: 2)
$X_6RKKX_7KKLX_8KKLSPVIPLLX_9X_{10}X_{11}$ wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is optionally C-terminally amidated; or a pharmaceutically acceptable salt thereof.

3. The antimicrobial peptide of clause 1, wherein the antimicrobial peptide comprises an amino acid sequence of (SEQ ID NO: 2)
$X_6RKKX_7KKLX_8KKLSPVIPLLX_9X_{10}X_{11}$ wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is C-terminally amidated; or a pharmaceutically acceptable salt thereof.

4. The antimicrobial peptide of clause 2, wherein the antimicrobial peptide comprises an amino acid sequence of (SEQ ID NO: 3)
$X_6RKKX_7KKLX_8KKLSPVIPLLX_9X_{10}X_{11}$ wherein $X_6$ is F, L or A, $X_7$ is F or L, $X_8$ is F or A, $X_9$ is H or K, $X_{10}$ is L, $X_{11}$ is G, and $X_{11}$ is optionally C-terminally amidated, provided that when $X_7$ is F, $X_6$ is L; or a pharmaceutically salt thereof.

5. The antimicrobial peptide of any one of clauses 1-4, wherein $X_7$ is L; or a pharmaceutically acceptable salt thereof.

6. The antimicrobial peptide of any one of clauses 1-5, wherein $X_9$ is K; or a pharmaceutically acceptable salt thereof.

7. The antimicrobial peptide of any one of clauses 1-3 or 5-6, wherein $X_{10}$ is L; or a pharmaceutically acceptable salt thereof.

8. The antimicrobial peptide of any one of clauses 1-3 or 5-7, wherein $X_{11}$ is G; or a pharmaceutically acceptable salt thereof.

9. The antimicrobial peptide of any one of clauses 1-8, wherein the antimicrobial peptide is C-terminally amidated.

10. The antimicrobial peptide of any one of clauses 1, 2, and 4 wherein $X_{11}$ is C-terminally amidated.

11. The antimicrobial peptide of clause 1, wherein the antimicrobial peptide comprises a sequence that is at least 90%, at least 93%, or at least 95% identical to a sequence selected from the group consisting of SEQ ID NO:4, SEQ ID NO:5, SEQ ID NO:6, SEQ ID NO: 7, SEQ ID NO: 8, SEQ ID NO: 9, and SEQ ID NO: 10; or a pharmaceutically acceptable salt thereof.

12. The antimicrobial peptide of clause 1, wherein the antimicrobial peptide comprises a sequence that is at least 90%, at least 93%, or at least 95% identical to a sequence selected from the group consisting of SEQ ID NO: 4, SEQ ID NO: 5, and SEQ ID NO: 6; or a pharmaceutically acceptable salt thereof.

13. The antimicrobial peptide of clause 1, wherein the antimicrobial peptide comprises a sequence that is at least 90%, at least 93%, or at least 95% identical to a sequence selected from the group consisting of SEQ ID NO: 7, SEQ ID NO: 8, SEQ ID NO: 9, and SEQ ID NO: 10; or a pharmaceutically acceptable salt thereof.

14. The antimicrobial peptide of clause 1, wherein the antimicrobial peptide comprises SEQ ID NO: 4; or a pharmaceutically acceptable salt thereof.

15. The antimicrobial peptide of clause 1, wherein the antimicrobial peptide comprises SEQ ID NO: 5; or a pharmaceutically acceptable salt thereof.

16. The antimicrobial peptide of clause 1, wherein the antimicrobial peptide comprises SEQ ID NO: 6; or a pharmaceutically acceptable salt thereof.

17. The antimicrobial peptide of clause 1, wherein the antimicrobial peptide comprises SEQ ID NO: 7; or a pharmaceutically acceptable salt thereof 18. The antimicrobial peptide of clause 1, wherein the antimicrobial peptide comprises SEQ ID NO: 8; or a pharmaceutically acceptable salt thereof 19. The antimicrobial peptide of clause 1, wherein the antimicrobial peptide comprises SEQ ID NO: 9; or a pharmaceutically acceptable salt thereof 20. The antimicrobial peptide of clause 1, wherein the antimicrobial peptide comprises SEQ ID NO: 10; or a pharmaceutically acceptable salt thereof 21. The antimicrobial peptide of any one of clauses 1-20 further comprising a reporter; or a pharmaceutically acceptable salt thereof.

22. The antimicrobial peptide of clause 21, wherein the reporter is a fluorophore; or a pharmaceutically acceptable salt thereof.

23. A pharmaceutically acceptable salt of any one of clauses 1-22.

24. An antimicrobial peptide comprising an amino acid sequence of (SEQ ID NO: 1)
$X_1X_2X_3X_4X_5X_6RKKX_7KKLX_8KKLSPVIPLLX_9X_{10}X_{11}-NH_2$ wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, $X_{11}$ is a non-polar amino acid or absent; and $X_{11}$ C-terminally amidated; or a pharmaceutically acceptable salt thereof.

25. The antimicrobial peptide of clause 24, wherein the antimicrobial peptide comprises an amino acid sequence of $$X_6RKKX_7KKLX_8KKLSPVIPLLX_9X_{10}X_{11}-NH_2 \quad (\text{SEQ ID NO: 2})$$

wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is C-terminally amidated; or a pharmaceutically acceptable salt thereof.

26. The antimicrobial peptide of clause 24, wherein the antimicrobial peptide comprises an amino acid sequence of $$X_6RKKX_7KKLX_8KKLSPVIPLLX_9X_{10}X_{11}-NH_2 \quad (\text{SEQ ID NO: 3})$$

wherein $X_6$ is F, L or A, $X_7$ is F or L, $X_8$ is F or A, $X_9$ is H or K, $X_{10}$ is L, $X_{11}$ is G, and $X_{11}$ is C-terminally amidated, provided that when $X_7$ is F, $X_6$ is L; or a pharmaceutically salt thereof.

27. The antimicrobial peptide of any one of clauses 24-26, wherein $X_7$ is L; or a pharmaceutically acceptable salt thereof.

28. The antimicrobial peptide of any one of clauses 24-27, wherein $X_9$ is K; or a pharmaceutically acceptable salt thereof.

29. The antimicrobial peptide of any one of clauses 24-25 or 27-28, wherein $X_{10}$ is L; or a pharmaceutically acceptable salt thereof.

30. The antimicrobial peptide of any one of clauses 24-25 or 27-29, wherein $X_{11}$ is G; or a pharmaceutically acceptable salt thereof.

31. The antimicrobial peptide of clause 24, wherein the antimicrobial peptide comprises a sequence that is at least 90%, at least 93%, or at least 95% identical to a sequence selected from the group consisting of SEQ ID NO: 4, SEQ ID NO: 5, SEQ ID NO: 6, SEQ ID NO: 7, SEQ ID NO: 8, SEQ ID NO: 9, and SEQ ID NO: 10; or a pharmaceutically acceptable salt thereof.

32. The antimicrobial peptide of clause 24, wherein the antimicrobial peptide comprises SEQ ID NO: 4; or a pharmaceutically acceptable salt thereof.

33. The antimicrobial peptide of clause 24, wherein the antimicrobial peptide comprises SEQ ID NO: 5; or a pharmaceutically acceptable salt thereof.

34. The antimicrobial peptide of clause 24, wherein the antimicrobial peptide comprises SEQ ID NO: 6; or a pharmaceutically acceptable salt thereof.

35. The antimicrobial peptide of clause 24, wherein the antimicrobial peptide comprises SEQ ID NO: 7; or a pharmaceutically acceptable salt thereof 36. The antimicrobial peptide of clause 24, wherein the antimicrobial peptide comprises SEQ ID NO: 8; or a pharmaceutically acceptable salt thereof 37. The antimicrobial peptide of clause 24, wherein the antimicrobial peptide comprises SEQ ID NO: 9; or a pharmaceutically acceptable salt thereof 38. The antimicrobial peptide of clause 24, wherein the antimicrobial peptide comprises SEQ ID NO: 10; or a pharmaceutically acceptable salt thereof 39. The antimicrobial peptide of any one of clauses 24-38 further comprising a reporter; or a pharmaceutically acceptable salt thereof.

40. The antimicrobial peptide of clause 39, wherein the reporter is a fluorophore; or a pharmaceutically acceptable salt thereof.

41. A pharmaceutically acceptable salt of any one of clauses 24-40.

42. A method of killing Gram-negative bacteria, the method comprising
contacting Gram-negative bacteria with an antimicrobial peptide comprising an amino acid according to any one of clauses 1-41; or a pharmaceutically acceptable salt thereof.

43. The method of clause 42, wherein the Gram-negative bacteria are a Enterobacteriacea bacteria.

44. The method of clause 42 or 43, wherein the Gram-negative bacteria are an *Escherichia*, an *Enterobacter*, a *Klebsiella*, a *Pseudomonas*, or a mixture thereof.

45. The method of any one of clauses 42-44, wherein the Gram-negative bacteria are an *Escherichia*, an *Enterobacter* species, or a mixture thereof.

46. The method of any one of clauses 42-44, wherein the Gram-negative bacteria are a *Klebsiella* species, a *Pseudomonas* species, or a mixture thereof.

47. The method of any one of clauses 42-46, wherein the Gram-negative bacteria are resistant to antibiotics.

48. The method of any one of clauses 42-47, wherein the Gram-negative bacteria are resistant to polymyxins.

49. The method of any one of clauses 42-48, wherein the Gram-negative bacteria are resistant to colistin.

50. The method of clause 42, wherein the Gram-negative bacteria are a member of the Enterobacteriacea family.

51. The method of clause 50, wherein the Enterobacteriacea comprises an *Escherichia coli*, an *Enterobacter cloacae*, a *Klebsiella pneumoniae*, a *Pseudomonas aeruginosa*, or a mixture thereof.

52. The method of any one of clauses 50 or 51, wherein the Gram-negative bacteria are antibiotic resistant.

53. The method of clause 52, wherein the antibiotic is a carbapenem or polymyxin.

54. The method of clause 53, wherein the polymyxin is colistin.

55 The method of clause 53, wherein the carbapenem is imipenem or meropenem.

56. The method of anyone of clauses 42-55, wherein the Gram-negative bacteria are in a biofilm.

57. The method of anyone of clauses 42-56, wherein the antimicrobial peptide is in a composition with an antibiotic.

58. A composition comprising an antimicrobial peptide from anyone of clauses 1-41 and an antibiotic.

59. A method of treating a Gram-negative bacterial infection in a subject in need thereof, the method comprising:
administering to the subject an effective amount of an antimicrobial peptide according to any one of clauses 1-41; or a pharmaceutically acceptable salt thereof.

60. The method of clause 59, wherein the Gram-negative bacterial infection is due to an *Escherichia* species, an *Enterobacter* species, or a mixture thereof.

61. The method of clause 59, wherein the Gram-negative bacterial infection is due to a *Klebsiella* species, a *Pseudomonas* species, or a mixture thereof.

62. The method of clause 59, wherein the subject is a mammal.

63 The method of clause 62, wherein the subject is a mouse or a human.

64. The method of clause 59, wherein the Gram-negative bacteria are an *Escherichia coli*, an *Enterobacter cloacae*, a *Klebsiella pneumoniae*, a *Pseudomonas aeruginosa*, or a mixture thereof.

65. The method of any one of clauses 59, 60, or 64, wherein the Gram-negative bacteria are *Enterobacter cloacae*.

66. A method of providing sterilization to raw seafood, the method comprising:
contacting a seafood source with an effective amount of at least one antimicrobial peptide of any one of clauses 1-41.

67. An antimicrobial compound comprising a peptide comprising an amino acid sequence of $$X_1X_2X_3X_4X_5X_6RKKX_7KKLX_8KKLSPVIPLLX_9X_{10}X_{11} \quad \text{(SEQ ID NO: 1)}$$

wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, and $X_{11}$ is a non-polar amino acid or absent; or a pharmaceutically acceptable salt thereof.

68. The antimicrobial compound of clause 67, wherein the peptide comprises an amino acid sequence of $$X_1X_2X_3X_4X_5X_6RKKX_7KKLX_8KKLSPVIPLLX_9X_{10}X_{11} \quad \text{(SEQ ID NO: 11)}$$

wherein $X_1$ is G or absent, $X_2$ is R or absent, $X_3$ is F, A, or absent, $X_4$ is K or absent, $X_5$ is R or absent, $X_6$ is F or L, $X_7$ is F or L, $X_8$ is F or A, $X_9$ is H, K, or absent, $X_{10}$ is L or absent, and $X_{11}$ is G or absent, provided that when $X_7$ is F, $X_6$ is L; or a pharmaceutically salt thereof.

69. The antimicrobial compound of clause 67, wherein the peptide comprises an amino acid sequence of $$X_1X_2X_3X_4X_5X_6RKKX_7KKLX_8KKLSPVIPLLX_9X_{10}X_{11} \quad \text{(SEQ ID NO: 11)}$$

wherein $X_7$ is F or L, provided that if $X_7$ is F, $X_6$ is not F; or a pharmaceutically salt thereof.

70. The antimicrobial compound of clause 67, wherein the peptide comprises a C-terminal modification, an N-terminal modification, or both an C-terminal modification and an N-terminal modification.

71. The antimicrobial compound of clause 70, wherein the peptide is N-terminally substituted to form RC(O)N(H)-peptide, wherein R is a —$OR^A$, —$NR^AR^B$, $C_{1-18}$ alkyl, or $C_{1-18}$ heteroalkyl, wherein each $R^A$ and $R^B$ is individually H, $C_{1-18}$ alkyl, or $C_{1-18}$ heteroalkyl, wherein each hydrogen atom on $C_{1-18}$ alkyl or $C_{1-18}$ heteroalkyl is optionally substituted with halo, hydroxy, or amino.

72. The antimicrobial compound of clause 70, wherein the peptide is C-terminally substituted to form (peptide)-C(O)R, wherein R is a —$OR^A$, —$NR^AR^B$, $C_{1-18}$ alkyl, or $C_{1-18}$ heteroalkyl, wherein each $R^A$ and $R^B$ is individually H, $C_{1-18}$ alkyl, $C_{1-18}$ heteroalkyl, or polyethylene glycol (PEG), wherein each hydrogen atom on $C_{1-18}$ alkyl or $C_{1-18}$ heteroalkyl is optionally substituted with halo, hydroxy, or amino, provided that when R is $OR^A$, $R^A$ is not H.

73. The antimicrobial compound of clause 67, wherein $X_7$ is L; or a pharmaceutically acceptable salt thereof.

74. The antimicrobial compound of clause 67, wherein the peptide comprises a sequence that is at least 90%, at least 93%, or at least 95% identical to a sequence selected from the group consisting of SEQ ID NOS: 1-11; or a pharmaceutically acceptable salt thereof.

75. A method of treating a Gram-negative bacterial infection in a subject in need thereof, the method comprising:
administering to the subject an effective amount of an antimicrobial compound according to clause 67; or a pharmaceutically acceptable salt thereof.

76. The method of clause 75, wherein the Gram-negative bacterial infection is due to an *Escherichia* species, an *Enterobacter* species, or a mixture thereof.

77. The method of clause 75, wherein the Gram-negative bacterial infection is due to a *Klebsiella* species, a *Pseudomonas* species, or a mixture thereof.

78. The method of clause 75, wherein the subject is a mammal.

79. The method of clause 78, wherein the subject is a mouse or a human.

80. The method of clause 75, wherein the Gram-negative bacteria are a member of the Enterobacteriacea family.

81. The method of clause 75, wherein the Gram-negative bacteria are resistant to antibiotics.

82. The method of clause 80, wherein the Enterobacteriacea is an *Escherichia coli*, an *Enterobacter cloacae*, a *Klebsiella pneumoniae*, a *Pseudomonas aeruginosa*, or a mixture thereof.

83. The method of clause 81, wherein the Gram-negative bacteria are resistant to polymyxins.

84. The method of clause 81, wherein the Gram-negative bacteria are resistant to colistin.

85. An antimicrobial compound comprising a peptide comprising an amino acid sequence of $$X_6RKKX_7KKLX_8KKLSPVIPLL \quad \text{(SEQ ID NO: 7)}$$

$X_6$ is a non-polar amino acid, $X_7$ is a non-polar amino acid, $X_8$ is a non-polar amino acid, provided that if $X_7$ is F, $X_6$ is not F, and wherein the N-terminus and the C-terminus of the amino acid sequence is optionally substituted.

86. The antimicrobial compound of clause 85, wherein the N-terminus, the C-terminus, or both the N-terminus and the C-terminus of the peptide is substituted.

87. The antimicrobial compound of clause 86, comprising a peptide selected from the group consisting of

```
                                    (SEQ ID NO: 4)
FRKKLKKLFKKLSPVIPLLKLG-NH2;

(SEQ ID NO: 5)
FRKKLKKLAKKLSPVIPLLKLG-NH2;

(SEQ ID NO: 6)
ARKKLKKLAKKLSPVIPLLKLG-NH2;

(SEQ ID NO: 8)
Ac-FRKKLKKLFKKLSPVIPLLKLG-NH2;

(SEQ ID NO: 9)
Ac-FRKKLKKLFKKLSPVIPLLKLG-PEG;
and (SEQ ID NO: 10)
PEG-FRKKLKKLFKKLSPVIPLLKLG-NH2;
``` or a pharmaceutically acceptable salt thereof.

88. A method of treating an infected wound, the method comprising contacting an infected wound with at least one antimicrobial peptide of clauses 1-41, and wherein the at least one antimicrobial peptide treats the infected wound.

89. A method of killing a *Vibrio cholerae*, the method comprising contacting the *Vibrio cholerae* with an antimicrobial peptide comprising an amino acid sequence selected from the group consisting of SEQ ID NO: 4, SEQ ID NO: 5, and SEQ ID NO 6, or a mixture thereof, and wherein the antimicrobial peptide kills the *Vibrio cholerae,*

90. A method of inhibiting the growth of a *Vibrio cholerae*, the method comprising contacting the *Vibrio cholerae* with a sub-lethal dose of an antimicrobial peptide comprising an amino acid sequence selected from the group consisting of SEQ ID NO: 4, SEQ ID NO: 5, and SEQ ID NO 6, or a mixture thereof, and wherein the antimicrobial peptide inhibits the growth of the *Vibrio cholerae,*

91. A pharmaceutically acceptable salt of any one of clauses 89-90.

BRIEF DESCRIPTIONS OF THE DRAWINGS

The detailed description particularly refers to the accompanying figures in which:

FIG. 1 shows a comparative amount of hemoglobin released by human red blood cells (hRBC) treated with 2 micromolar (μM) of antimicrobial peptides.

FIG. 2 shows the release of hemoglobin from human red blood cells (hRBC), treated with antimicrobial peptides, as a function of peptide concentration.

FIG. 3 is a graph showing of peptide B22 (mock), B22a and B22m1 (each at 30 nM) can reduce bacterial growth of *P. aeruginosa*, wherein the bacteria were grown in a plate reader at 37° Celsius and shaken. Optical density was monitored every ten (10) minutes to track the growth rate.

FIG. 4 is a bar graph showing the quantification of cell division time for *E. coli* UTI198 and *Enterobacter cloacae* OC4080 in the presence of 100 nanomolar (nM) B22a, and further showing that B22a increased the cell division time by more than 2-fold.

FIG. 5 shows the efficacy and toxicity of modified peptides (AB22N (SEQ ID NO: 7); AB22P (SEQ ID NO: 9); and PB22N (SEQ ID NO: 10)) on mice survival, wherein the survival of mice injected intraperitoneally with iron dextran at 48 h after intraperitoneal injection of 10 or 20 μM of the modified peptides is shown.

FIG. 6 is an image showing *V. cholerae* cells fluorescently labeled for live or dead, wherein the top row shows a mock-treated group and the bottom row is treated with 100 nM of B22, and wherein the bacteria treated with B22 begin to die and the proportion of dead cells increases overtime without the addition of more antimicrobial peptide.

FIG. 7 is a graph quantifying the total biomass of *V. cholerae* mock-treated (black bars) and treated (white bars) with B22, and the percent of dead cells within the biofilms (untreated, black circles; treated, white circles).

FIG. 8 is an image showing *V. cholerae* cells fluorescently labeled for live or dead, wherein the top row shows a mock-treated group and the bottom row is treated with 100 nM of B22a, and wherein the bacteria treated with B22a begin to die and the amount of death increases overtime without the addition of more antimicrobial peptide.

FIG. 9 is a graph quantifying the total biomass of *V. cholerae* growing in biofilm that are mock-treated (black bars) or treated (white bars) with B22a, and the percent of dead cells within the biofilms (untreated, black circles; treated, white circles).

FIG. 10 is a graph showing the inhibition of growth of *E. coli* 25922 after addition of a sub-lethal dose of mock, B22, and B22a at a concentration of 30 nM each over time.

FIG. 11 is a graph showing the inhibition of growth of *E. cloacae* 4080 after addition of a sub-lethal dose of mock, B22, and B22a at a concentration of 30 nM each over time.

FIG. 12 is a graph showing that treatment with B22a can increase the cell division time of bacteria, consistent with a reduction in their growth rate, and wherein *E. coli* and *E. cloacae* were incubated without or with 30 nM B22a and cell division time was recorded by time-lapse phase contrast microscopy.

FIG. 13 is a graph showing the growth rate of *P. aeruginosa* PAO1 was reduced by both 30 nM of B22a and B22m1, wherein both B22a and B22m1 have MICs of 2 μM for *P. aeruginosa* PAO1.

BRIEF DESCRIPTIONS OF THE SEQUENCES

SEQ ID NO: 1
$X_1X_2X_3X_4X_5X_6RKKX_7KKLX_8KKLSPVIPLLX_9X_{10}X_{11}$

SEQ ID NO: 2
$X_6RKKX_7KKLX_8KKLSPVIPLLX_9X_{10}X_{11}$

SEQ ID NO: 3
$X_6RKKX_7KKLX_8KKLSPVIPLLX_9X_{10}X_{11}$

B22a
SEQ ID NO: 4
$FRKKLKKLFKKLSPVIPLLKLG-NH_2$

B22m1
SEQ ID NO: 5
$FRKKLKKLAKKLSPVIPLLKLG-NH_2$

B22m2
SEQ ID NO: 6
$ARKKLKKLAKKLSPVIPLLKLG-NH_2$

SEQ ID NO: 7
$X_6RKKX_7KKLX_8KKLSPVIPLL$

AB22a
SEQ ID NO: 8
Acetyl-FRKKLKKLFKKLSPVIPLLKLG-amide

AB22P
SEQ ID NO: 9
Acetyl-FRKKLKKLFKKLSPVIPLLKLG-minipolyethylene glycol

PB22N
SEQ ID NO: 10
minipolyethylene glycol-PRKKLKKLFKKLSPVIPLLKLG-amide

SEQ ID NO: 11
$X_1X_2X_3X_4X_5X_6RKKX_7KKLX_8KKLSPVIPLLX_9X_{10}X_{11}$

B22
SEQ ID NO: 12
FRKKLKKLFKKLSPVIPLLKLG

DETAILED DESCRIPTION

Unless defined otherwise, the scientific and technology nomenclatures have the same meaning as commonly understood by a person of ordinary skill in the art pertaining to this disclosure.

In some embodiments, an antimicrobial peptide comprises an amino acid sequence of $X_1X_2X_3X_4X_5X_6RKKX_7KKLX_8KKLSPVIPLLX_9X_{10}X_{11}$ (SEQ ID NO: 1), wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, and $X_{11}$ is a non-polar amino acid or absent; or a pharmaceutically acceptable salt thereof. In some embodiments, the peptide may comprise as C-terminal modification. In some embodiments, the peptide may be C-terminally amidated. In some embodiments, the peptide may comprise an N-terminal modification.

In some embodiments, an antimicrobial peptide comprises an amino acid sequence of $X_6RKKX_7KKLX_8KKLSPVIPLLX_9X_{10}X_{11}$ (SEQ ID NO: 2), wherein $X_6$ is a non-polar amino acid, $X_7$ is a non-polar amino acid, $X_8$ is a non-polar amino acid, $X_9$ is a basic amino acid, $X_{10}$ is a non-polar amino acid, and $X_{11}$ is a non-polar amino acid; or a pharmaceutically acceptable salt thereof. In some embodiments, the peptide may comprise as C-terminal modification. In some embodiments, the peptide may have a C-terminal amidate. In some embodiments, the peptide may comprise an N-terminal modification.

In some embodiments, an antimicrobial peptide comprises an amino acid sequence of $X_6RKKX_7KKLX_8KKLSPVIPLLX_9X_{10}X_{11}$ (SEQ ID NO: 3), wherein $X_6$ is F or L, $X_7$ is F or L, $X_8$ is F or A, $X_9$ is H or K, $X_{10}$ is L, and $X_{11}$ is G, provided that when $X_7$ is F, $X_6$ is L; or a pharmaceutically salt thereof. In some embodiments, the peptide may comprise a C-terminal chemical modification. In some embodiments, the peptide may have a C-terminal amidate. In some embodiments, the peptide may comprise an N-terminal modification.

In some embodiments, an antimicrobial peptide comprises an amino acid sequence selected from the group consisting of SEQ ID NOs: 1-11, and a combination thereof. In some embodiments, the peptide may comprise a C-terminal chemical modification. In some embodiments, the peptide may have a C-terminally amidate. In some embodiments, the peptide may comprise an N-terminal chemical modification.

Previous studies have provided knowledge on how to engineer some of the natural cathelicidins into a more potent bacteria-killing agent, yet have reduce toxicity to human cells relative to that the natural peptides. A detailed description and list of such engineered peptides are found in the PCT International Application No. PCT/US16/63612, filed on Nov. 23, 2016, the disclosure of which is hereby incorporated by reference in its entirety.

Several non-naturally occurring antimicrobial peptides have been generated and tested as described herein. Antimicrobial peptides in accordance with the present disclosure are efficient at killing a number of foodborne Gram-negative bacteria. In some embodiments, the Gram-negative bacteria are particularly those found in the Enterobacteriacea family. In some embodiments, the antimicrobial peptide has reduced cytotoxicity for human cells. For example, a low concentration of an antimicrobial peptide in accordance with the present disclosure may effectively kill various Gram-negative bacteria. When selective peptides are tested for their bacterial killing effects, the colony forming units for various Gram-negative bacteria, including *E. cloacae* 4080, *E. coli* IU 342, *K. pneumonia* 8893, and *K. pneumoniae* C-2 were reduced within minutes of exposure to the antimicrobial peptide. The fold change can be from hundreds to thousands of folds reduction. The antimicrobial peptides described herein may be used to treat or kill *V. cholera*. In some embodiments, *V. cholera* may be killed or growth inhibited by contacting the *V. cholera* with an effective amount of an antimicrobial peptide comprising an amino acid sequence selected from the group SEQ ID NO: 4, SEQ ID NO: 5, SEQ ID NO: 6, a mixture thereof, or a pharmaceutically acceptable salt.

As one skilled in the art will appreciate, in some embodiments the antimicrobial peptides are degradable to become non-toxic amino acids. It is contemplated that these antimicrobial peptides can be used to treat raw seafood or liquids comprising a Gram-negative bacterium.

In some embodiments, the antimicrobial peptides may be used to treat aquaculture. These antimicrobial peptides can also be used in the fish pond to prevent or cure infections in farm-raised fish or shellfish, etc. One advantage of such use is that the peptides do not need to be removed after the treatment since it can be degraded into non-toxic amino acid. Thus, the application of these identified antimicrobial peptides (or the variants thereof that possess the similar bacterial killing effect) can become a useful tool in the food processing industry. The peptides produced in this disclosure can also be used to decrease the bacterial load and render uncooked shellfish and fish safer for consumption.

In some embodiments, antimicrobial peptides in accordance with the present disclosure can be used to treat farm-harvested or wild-caught seafood. Illustratively, the seafood may be a fish or a shellfish. Illustrative shellfish include crabs, prawns, oysters, and clams.

In some embodiments, antimicrobial peptides in accordance with the present disclosure can be used to treat an infection in a subject. In some embodiments, the infection is in a wound. In some embodiments, the infected wound may be treated by contacting the infected wound with a composition comprising an antimicrobial peptide or a pharmaceutically acceptable salt thereof.

In some embodiments, the antimicrobial peptides and variants thereof kill Gram-negative bacteria within minutes and effectively (with several orders of magnitude) reduce viable bacterial numbers. The mechanism of action is likely due to perforation of the bacterial membrane. The reduction in viable bacterial number will decrease the infection of the aquaculture product to decrease infection of consumers of the aquaculture product. Application of these anti-microbial peptides in seafood preparation and aquafarming is contemplated within this disclosure.

Antimicrobial peptides and variants thereof may comprise polar amino acids. In some embodiments, polar amino acids are selected from the group consisting of asparagine (Asn, N), cysteine (Cys, C), glutamine (Gln, Q), serine (Ser, S), threonine (Thr, T), and tyrosine (Tyr, Y). It should be understood that acceptable polar amino acid variants include D-amino acids, peptoids, synthetic peptides, and any suitable alternative thereof.

Antimicrobial peptides and variants thereof may comprise non-polar amino acids. In some embodiments, the non-polar amino acids are selected from the group consisting of alanine (Ala, A), glycine (Gly, G), isoleucine (Ile, I), leucine (Leu, L), methionine (Met, M), phenylalanine (Phe, F), proline (Pro, P), tryptophan (Trp, W), and valine (Val, V). It should be understood that acceptable non-polar amino acid variants include D-amino acids, peptoids, synthetic peptides, and any suitable alternative thereof.

Antimicrobial peptides and variants thereof may comprise basic amino acids. In some embodiments, the basic amino acids are selected from the group consisting of arginine (Arg, R), lysine (Lys, K), and histidine (His, H). In some embodiments, the basic amino acids comprise functional groups capable of being positively charged at physiological pH. Representative basic functional groups include amines, guanidines, and heteroaromatic rings capable of being ionized at physiological pH. It should be understood that acceptable basic amino acid variants include D-amino acids, peptoids, synthetic peptides, and any suitable alternative thereof.

Antimicrobial peptides and variants thereof may comprise acidic amino acids. In some embodiments, acidic amino acids are selected from aspartic acid (Asp, D) glutamic acid (Glu, E), and derivatives thereof. In some embodiments, acidic amino acids comprise carboxylates or any other common functional group that is negatively-charged at physiological pH. It should be understood that acceptable acidic amino acid variants include D-amino acids, peptoids, synthetic peptides, and any suitable alternative thereof.

Antimicrobial peptides may comprise modified residues. In some embodiments, the antimicrobial peptide may comprise a C-terminal modification, an N-terminal modification, or both. In some embodiments, the C-terminal modification is a C-terminal amidation such as $C(O)NH_2$ as opposed to the carboxylic acid $C(O)OH$.

In some embodiments, the antimicrobial peptide comprises C-terminal modification such as a C-terminal amide. Illustratively, a C-terminal amide may be represented in a formula as Xaa-$NH_2$, where Xaa is any amino acid, unnatural amino acid, or derivative thereof. In some embodiments, if the antimicrobial peptide has a C-terminal glycine, the C-terminal amidation may be represented as G-$NH_2$.

In some embodiments, the C-terminus of the peptide is substituted to form (peptide)-C(O)R, wherein R is a —$OR^A$, —$NR^AR^B$, $C_{1-18}$ alkyl, or $C_{1-18}$ heteroalkyl, wherein each $R^A$ and $R^B$ is individually H, $C_{1-18}$ alkyl, $C_{1-18}$ heteroalkyl, or polyethylene glycol (PEG), wherein each hydrogen atom on $C_{1-18}$ alkyl or $C_{1-18}$ heteroalkyl is optionally substituted with halo, hydroxy, or amino, provided that when R is $OR^A$, $R^A$ is not H. In some embodiments, $C_{1-18}$ alkyl includes methyl, ethyl, and straight chained or branched propyl, butyl, pentyl, hexyl, or heptyl. In some embodiments $C_{1-18}$ alkyl is methyl. In some embodiments, $C_{1-18}$ heteroalkyl is a PEG. In some embodiments, $C_{1-18}$ heteroalkyl is 8-amino 3,6-dioxaoctanyl.

In some embodiments, the N-terminus of the peptide is substituted to form RC(O)N(H)-peptide, wherein R is a —$OR^A$, —$NR^AR^B$, $C_{1-18}$ alkyl, or $C_{1-18}$ heteroalkyl, wherein each $R^A$ and $R^B$ is individually H, $C_{1-18}$ alkyl, or $C_{1-18}$ heteroalkyl, wherein each hydrogen atom on $C_{1-18}$ alkyl or C1-18 heteroalkyl is optionally substituted with halo, hydroxyl, or amino groups. In some embodiments, $C_{1-18}$ alkyl includes methyl, ethyl, and straight chained or branched propyl, butyl, pentyl, hexyl, or heptyl groups. In some embodiments C1-18 alkyl is a methyl group. In some embodiments, C1-18 heteroalkyl is a PEG. In some embodiments, C1-18 heteroalkyl is 8-amino 3,6-dioxaoctanyl.

In some embodiments, the antimicrobial peptide is configured to minimize the formation of higher order structures. Illustratively, the antimicrobial peptide may be configured so that formation of multi-subunit structures or oligomers are minimized Illustratively, substituting a hydrophobic aromatic amino acid for a hydrophobic aliphatic amino acid or alanine may minimize the formation of multi-subunit structures or oligomers. In some embodiments, an antimicrobial peptide may have 1, 2, or 3 phenylalanines replaced with alanines. In some embodiments, minimizing the formation of a higher order structure or oligomers may allow the antimicrobial peptide to be effective at lower concentrations.

In some embodiments, peptides, sometimes called antimicrobial peptides, kill Gram-negative bacteria. In some embodiments, the Gram-negative bacteria are members of the Enterobacteriacea family. In some embodiments, the Gram-negative bacteria are *Enterobacter cloacae*. In other embodiments, the Enterobacteriacea comprise, consist essentially of, and/or consist of an *Escherichia coli*, an *Enterobacter cloaca*, a *Klebsiella pneumoniae*, a *Pseudomonas aeruginosa*, or a mixture thereof.

In some embodiments, an antimicrobial compound is provided. The antimicrobial compound comprising an amino acid sequence of SEQ ID NO: 1-11. In some embodiments, the antimicrobial compound further comprises a C-terminal modification, an N-terminal modification, or both a C-terminal modification and an N-terminal modification. In some embodiments, the C-terminus of the peptide is substituted to form (peptide)-C(O)R, wherein R is a —$OR^A$, —$NR^AR^B$, C1-18 alkyl, or C1-18 heteroalkyl, wherein each $R^A$ and $R^B$ is individually H, $C_{1-18}$ alkyl, $C_{1-18}$ heteroalkyl, or polyethylene glycol (PEG), wherein each hydrogen atom on $C_{1-18}$ alkyl or $C_{1-18}$ heteroalkyl is optionally substituted with halo, hydroxy, or amino, provided that when R is $OR^A$, $R^A$ is not H. In some embodiments, $C_{1-18}$ alkyl includes methyl, ethyl, and straight chained or branched propyl, butyl, pentyl, hexyl, or heptyl. In some embodiments $C_{1-18}$ alkyl is methyl. In some embodiments, $C_{1-18}$ heteroalkyl is a PEG. In some embodiments, $C_{1-18}$ heteroalkyl is 8-amino 3,6-dioxaoctanyl. In some embodiments, the N-terminus of the peptide is substituted to form RC(O)N(H)-peptide, wherein R is a —$OR^A$, —$NR^AR^B$, $C_{1-18}$ alkyl, or $C_{1-18}$ heteroalkyl, wherein each $R^A$ and $R^B$ is individually H, C1-18 alkyl, or C1-18 heteroalkyl, wherein each hydrogen atom on C1-18 alkyl or $C_{1-18}$ heteroalkyl is optionally substituted with halo, hydroxy, or amino. In some embodiments, C1-18 alkyl includes a methyl, ethyl, straight chained, or branched propyl, butyl, pentyl, hexyl, or heptyl groups. In some embodiments C1-18 alkyl is a methyl group. In some embodiments, $C_{1-18}$ heteroalkyl is a PEG. In some embodiments, $C_{1-18}$ heteroalkyl is 8-amino 3,6-dioxaoctanyl.

In other embodiments of the methods described herein, pharmaceutically acceptable salts of the compositions described herein are provided. Pharmaceutically acceptable salts of compositions described herein include acid addition and base salts thereof.

Suitable acid addition salts of the compositions described herein are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the compositions described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In yet other embodiments, pharmaceutical formulations are provided. Illustratively, a pharmaceutical formulation comprises a peptide, sometimes called an antimicrobial peptide, described in accordance with the present disclosure. In one illustrative embodiment, the pharmaceutical formulation comprises any of the pharmaceutical compositions described herein. The previously described embodiments of the pharmaceutical compositions are applicable to the pharmaceutical formulations described herein.

The type of formulation employed for the administration of the compounds, sometimes called a peptide or an antimicrobial peptide, may be dictated by the particular compounds employed, the type of pharmacokinetic profile desired from the route of administration and the compound(s), and the state of the patient. The peptides may be formulated as pharmaceutical compositions for systemic administration. Such pharmaceutical compositions and processes for making the same are known in the art for both humans and non-human mammals.

In some embodiments, the pharmaceutical formulations described herein further comprise a pharmaceutically acceptable carrier. In some embodiments, the pharmaceutical formulations described herein further comprise a pharmaceutically acceptable diluent. Diluent or carrier ingredients used in the pharmaceutical compositions containing peptides can be selected so that they do not diminish the desired effects of the peptide. Examples of suitable dosage forms include aqueous solutions of the peptides, for example, a solution in isotonic saline, 5% glucose or other well-known pharmaceutically acceptable liquid carriers such as alcohols, glycols, esters, and amides.

As used herein, "carrier" refers to any ingredient other than the active component(s) in a formulation. Pharmaceutically acceptable carriers are determined in part by the particular composition being administered, as well as by the particular method used to administer the composition. The choice of carrier will to a large extent depend on factors such as the particular mode of administration, the effect of the carrier on solubility and stability, and the nature of the dosage form. In one illustrative aspect, the carrier is a liquid carrier.

As used herein, the term "pharmaceutically acceptable" includes "veterinarily acceptable", and thus includes both human and animal applications independently. For example, a "patient" as referred to herein can be a human patient or a veterinary patient, such as a domesticated animal (e.g., a pet) or a food animal.

In some embodiments, the pharmaceutical formulations described herein optionally include one or more other therapeutic ingredients. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with the described peptides and may be either administered separately or in the same pharmaceutical formulation. The amount of other active ingredients to be given may be readily determined by one skilled in the art based upon therapy with described peptides.

In some embodiments, the pharmaceutical formulations described herein are a single unit dose. As used herein, the term "unit dose" is a discrete amount of the composition comprising a predetermined amount of the described peptides. The amount of the described peptides is generally equal to the dosage of the described peptides which would be administered to an animal or a convenient fraction of such a dosage such as, for example, one-half or one-third of such a dosage.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The aqueous preparations according to the invention can be used to produce lyophilisates by conventional lyophilization or powders. The preparations according to the invention are obtained again by dissolving the lyophilisates in water or other aqueous solutions. The term "lyophilization," also known as freeze-drying, is a commonly employed technique for presenting proteins which serves to remove water from the protein preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve the stability of the lyophilized product upon storage.

In some embodiments, the peptides in accordance with the present disclosure are described as antimicrobial peptides. In one embodiment, the solubility of the antimicrobial peptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a peptide may be formulated as a solid, semi-solid, or thixotropic liquid for administration as an implanted depot providing modified release of the active compound.

In other various embodiments, the administration according to the described methods is performed as a single dose administration. In other embodiments, the administration according to the described methods is performed as a multiple dose administration.

The formulations can be presented in unit-dose or multi-dose sealed containers, such as ampules and vials. The formulations can also be presented in syringes, such as prefilled syringes.

In various embodiments, the dosages of the antimicrobial peptides can vary significantly depending on the patient condition and the severity of the disease to be treated. The effective amount to be administered to a patient is based on body surface area, patient weight or mass, and physician assessment of patient condition.

As used herein, the term "effective amount" refers to an amount of an antimicrobial peptide, peptide, drug, or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the effective amount is that amount of an active which may treat or alleviate the disease or symptoms of the disease at a reasonable benefit/risk ratio applicable to any medical treatment. In another aspect, the effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effects, that might occur during administration of one or more of the antimicrobial peptides described herein. Further, it is appreciated that the co-therapies described herein may allow for the administration of lower doses of antimicrobial peptides that show such toxicity, or other undesirable side effects, where those lower doses are below thresholds of toxicity or lower in the therapeutic window than would otherwise be administered in the absence of a co-therapy.

As used herein, "administering" includes all means of introducing the antimicrobial peptides and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The antimicrobial peptides and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the antimicrobial peptides described herein, or pharmaceutically acceptable salts, solvates, hydrates thereof, with other chemical components, such as pharmaceutically acceptable excipients. The purpose of a pharmaceutical composition is to facilitate administration of an antimicrobial peptide to a subject. Pharmaceutical compositions suitable for the delivery of antimicrobial peptides described and methods for their preparation will be readily apparent to those skilled in the art. Such compositions and methods for their preparation may be found, for example, in 'Remington's Pharmaceutical Sciences', 19th Edition (Mack Publishing Company, 1995).

Suitable dosages of the antimicrobial peptides can be determined by standard methods, for example by establishing dose-response curves in laboratory animal models or in humans in clinical trials. Illustratively, suitable dosages of antimicrobial peptides (administered in a single bolus or over time) include from about 1 pg/kg to about 10 µg/kg, from about 1 pg/kg to about 1 µg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 µg/kg, from about 1 ng/kg to about 500 ng/kg, from about 100 ng/kg to about 500 µg/kg, from about 100 ng/kg to about 100 pg/kg, from about 1 µg/kg to about 500 µg/kg, or from about 1 µg/kg to about 100 µg/kg. In each of these embodiments, dose/kg refers to the dose per kilogram of a patient's or animal's mass or body weight.

The make and use of these peptides to sterilize raw fish and shellfish for food consumption are within the scope of the protection.

This disclosure identifies effective compositions for killing bacteria. In some embodiments, the bacteria are foodborne bacteria. In some embodiments, the bacteria are foodborne bacteria found in seafood. In some embodiments, these compositions are selected from the peptides group consisting of SEQ ID NOS: 1-11, particularly, SEQ ID NOs: 4-6 and 8-10.

Materials and Methods

Cells and reagents—The BEAS-2B cell line (a human lung epithelial cell line that expresses multiple Toll-like Receptors and can release proinflammatory cytokines in response to their activation) was from the American Type Culture Collection and cultured in BEGM media with its supplements (11; Lonza). Peptides without or with covalently attached fluorophores were custom synthesized (Karybaybio) and purified to at least 95% purity. siRNAs specific to FPRL1 (sc-40123), EGFR (sc-29301), or a non-specific control siRNA (sc-37007) were acquired from Santa Cruz Biotechnology.

Quantification of IL-6—IL-6 production was quantified by ELISA using the OptEIA™ kit (BD Biosciences). A typical assay used $2 \times 10^4$ BEAS-2B cells/well grown for 24 h in flat-bottom 96-well plates. Poly(I:C) was added to a final concentration of 0.13 µg/ml.

MIC determination—Antimicrobial activity was determined using the broth microdilution method based on the general recommendation of the Clinical and Laboratory Standards Institute. Bacteria were grown in Mueller-Hinton broth at 37° C. until $OD_{625}$ reached 0.06, and then bacteria were further diluted into 1:20 for later use. Peptides were diluted in Mueller-Hinton II broth at concentrations of 1, 2, 4, 8, 16, and 32 µg/ml. 10 microliter (µL) of diluted bacteria was mixed with 90 µL of peptides at varying concentrations followed by incubation at 37° C. for 16-18 hours. The MIC is the lowest peptide concentration at which visible growth was inhibited. The MIC value was determined at least twice in independent experiments and typically in 3-4 assays.

Hemolytic activity—The hemolytic activities of peptides were determined using human red blood cells (hRBCs) (Innovative Research, Inc., cat. #IPLA-WB3-18103). The hRBCs were washed three times with phosphate-buffered saline (PBS) and then resuspended in PBS. The hRBCs solution was mixed with serial dilutions of the peptides in PBS buffer. The reaction mixtures were incubated for 45 min at 37° C. After centrifugation at 94×g for 10 min, the intact hRBCs were pelleted and the hemoglobin released from hRBCs was monitored by measuring the absorbance of the supernatant at 415 nm. The background level of absorbance was measured in sampled incubated with only PBS buffer. 100% hemolysis was determined in sampled incubated with water. The percentage of hemolysis was calculated according to the following equation.

Percentage of hemolysis=$[(A_{sample}-A_{blank})/A_{water}]*100\%$

Enterobacteriacea killing activity—Enterobacteriacea bacteria such as *Enterobacter cloacae* were cultured in MH II broth at 30° C. The *Enterobacter cloacae* culture was diluted (e.g., 40×-200× diluted). Peptides at concentrations of 0.1 µM, 0.5 µM, 1 µM and/or 2 µM were prepared. The peptides were incubated with the bacteria for 1 hour at 30° C. before plated into the bacteria culture (100 µL peptides and 20 µL mock). The cultures were incubated overnight and Colony Forming Units (CFUs) were counted.

The high efficiency of bacterial killing and the low toxicity of these peptides provide insights to alternative solutions to serve food processing industry and aquafarming, which is of great value to the entire consumer industry.

EXAMPLES

The following examples present features, aspects and advantages of the present invention. They are for illustrative purposes only. Any and all changes and modifications that come within the spirit of the disclosure are desired to be protected.

Example 1: Identification of B22

B22 (SEQ ID NO: 12) was generated following the protocol described in U.S. Patent Application Publication 2019/0054140 A1. Briefly, bactericidal peptides shorter than BMAP-27B that retain the activities of these peptides were generated. The reduced length should decrease the cost of synthesis and increase the efficiency of synthesis. The sequence of BMAP-27B was used to generate a series of truncated peptides. Several of the peptides with truncations and amino acids substitutions were generated and tested for the killing of colistin-resistant *E. coli*, Top10pHNSHP45. B22 was found to have improved bactericidal activity relative to BMAP-27B. B22, which lacks 5 residues at the N-terminal region of BMAP-27B and reduced the number of viable colonies relative to BMAP27B. B22 had improved MIC against the majority of the 19 strains of Gram-negative bacteria used to select for effective cathelicidins.

Example 2: B22a Inhibits Gram-Negative Bacteria Growth

The C-terminus of natural peptides typically contain a carboxyl group that could affect interaction with negatively-charged phospholipids. Therefore, to eliminate the carboxyl group, the B22 peptide was synthesized with a C-terminal amide, resulting in a peptide named B22a (SEQ ID NO. 4). B22a was tested against 20 strains of Gram-negative bacteria using the broth dilution assay to determine the minimal inhibitory concentration (MIC). B22a was improved for inhibiting the majority of the Gram-negative bacteria of the Enterobacteriacea, including *Enterobacter cloacae, Escherichia coli, Pseudomonas aeruginosa,* and *Klebsiella pneumoniae* (Table 1). *Serratia marcescens*, which was shown to not be sensitive to the progenitors of B22, remain insensitive to B22a.

TABLE 1

C-terminally amidated B22 results in more effective inhibition of bacterial growth.

| | | Minimal inhibitory concentration (mM) | | |
|---|---|---|---|---|
| Species | Strain | BMAP-27B | B22 | B22a |
| Enterobacter cloacae | OC4080 | 4* | 4 | 4 |
| Enterobacter cloacae | OC4092 | 4 | 4 | 4 |
| Escherichia coli | ATCC 25922 | 4 | 2 | 2 |
| Escherichia coli | ATCC 35218 | 4 | 4 | 2 |
| Escherichia coli | IU342 | 2 | 4 | 2 |
| Escherichia coli | J53 AzideR | 4 | 4 | 2 |
| Escherichia coli | OC4075 | 4 | 4 | 2 |
| Escherichia coli | MC4100a | 4 | 4 | 4 |
| Escherichia coli | UTI89 | 4 | 2 | 2 |
| Klebsiella pneumonia | ATCC 700603 | 4 | 2 | 2 |
| Klebsiella pneumonia | C2 | 4 | 4 | 2 |
| Klebsiella pneumonia | OC4110 | 8 | 4 | 2 |
| Klebsiella pneumonia | OC8893 | 8 | 4 | 2 |
| Pseudomonas aeruginosa | ATCC 27853 | 4 | 4 | 2 |
| Pseudomonas aeruginosa | OC4083 | 4 | 2 | 2 |
| Pseudomonas aeruginosa | PAO1 | 4 | 4 | 2 |
| Pseudomonas aeruginosa | PAO1 oprD | 4 | 4 | 2 |
| Serratia marcescens | 4075A | 16 | >32 | NT |
| Serratia marcescens | 4101 | 16 | >32 | >32 |
| Serratia marcescens | 4104 | 16 | >32 | >32 |

Example 3: B22a Inhibits Gram-Negative Bacteria Growth

The broth dilution assay tested for the inhibition of growth. To determine whether B22a has bactericidal activity, viable colonies that formed after bacteria were treated with 2 μM of B22a for 30 min were enumerated (Table 2). Peptide B22a reduced viable colony formation by *E. coli* by over 2 orders of magnitude. B22a reduced viable colony formation by *P. aeruginosa* by over 3 orders of magnitudes. B22a, like its predecessor B22, is bactericidal for Gram-negative bacteria at the minimal inhibitory concentration.

TABLE 2

Bactericidal activity of B22a and other C-terminally amidated peptides on *E. coli* and *P. aeruginosa* viable colony formation.

| | E. coli ATCC 25922 | Fold reduction | P. aeruginosa PAO1 | Fold reduction |
|---|---|---|---|---|
| Mock | $8 \times 10^5$ | 1 | $1.2 \times 10^5$ | 1 |
| B22a | $1.3 \times 10^3$ | 615 | <20 | >6000 |
| B22m1 | $4.7 \times 10^3$ | 170 | <20 | >6000 |
| B22m2 | $8.7 \times 10^4$ | 9 | $7.3 \times 10^3$ | 164 |

Example 4: B22a Affects Antibiotic Resistant Bacteria

Antibiotic resistant Enterobacteriacea is a growing concern. Resistant bacteria have recently overcome the two lines of antibiotics that have been put in reserve for use only when necessary: carbapenems and polymyxins. *Klebsiella pneumoniae* is especially concerning, as strains isolated from patients have been documented to become resistant to either or both carbapenems and the polymyxin named colistin. Since B22a can effectively kill members of the Enterobacteriacea, B22a was tested against 20 clinical isolates of *K pneumoniae* that have been characterized for resistance to carbapenems (imipenem or meropenem) and/or Colistin. For all 19 of the 20 clinical isolates strains, the minimal inhibitory concentrations of B22a appear to be unchanged from *K. pneumoniae* that have not acquired drug resistance. The remaining strain, Isolate 361, had only a two-fold increase in the MIC value. These results show that B22a is capable of inhibiting multi-drug resistant clinical isolates of *K. pneumoniae*.

Example 5: B22a does not Significantly Increase Human Red Blood Cell Lysis

The increased efficacy of B22a to kill bacteria raises the possibility that it is also capable of interacting with mammalian cells and cause cell damage. Mammalian cells are thought to be less susceptible to cathelicidin peptides in part because the composition of their membrane will be less likely to interact with the peptides. To address this directly, human red blood cells (hRBCs) were tested for lysis after a 45-minute incubation with the peptides. The total lysis of hRBCs was determined by adding water to the cells. The amount of lysis during handling was determined by the addition of phosphate buffered saline at the same volume as that of the peptides. At a final concentration of 2 micromolar of LL-37 (cathelicidin from humans), a low abundance of hemoglobin outside of the cells was detected (FIG. 1). B22, B22a, BMAP-27B (modifications on cathelicidin from cows), and ShpC (cathelicidin from sheep) all caused a minimal amounts of hemoglobin release from hRBCs.

Figure 2:
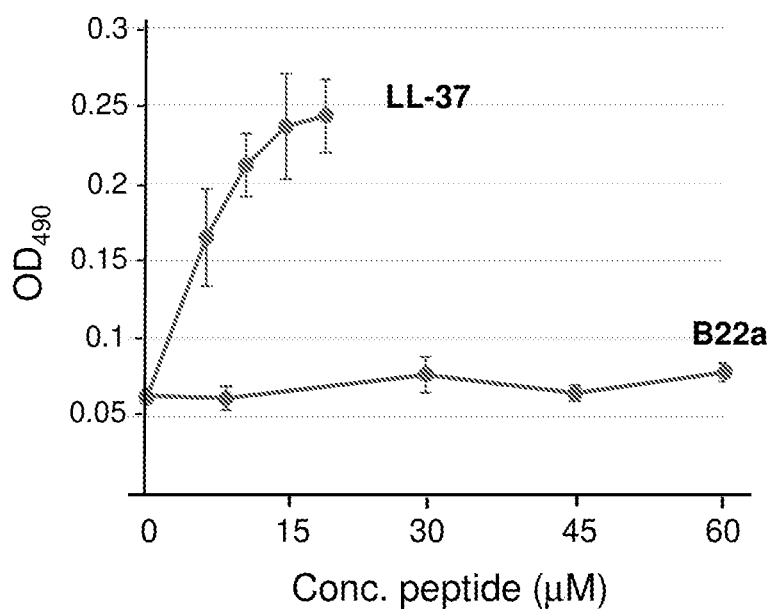

To better assess hRBC lysis, increasing concentrations of the peptides were added. LL-37 resulted in significantly higher hRBC lysis as its concentration increased to beyond a final concentration of 10 micromolar (FIG. 2). In contrast, B22a did not significantly increase hRBC lysis at even a final concentration of 60 micromolar (FIG. 2). These results suggest that the chemically modified B22a can selectively target bacteria without significantly harmful effects on human red blood cells.

Example 6: B22a Kills Bacteria in Biofilms

Figure 3:
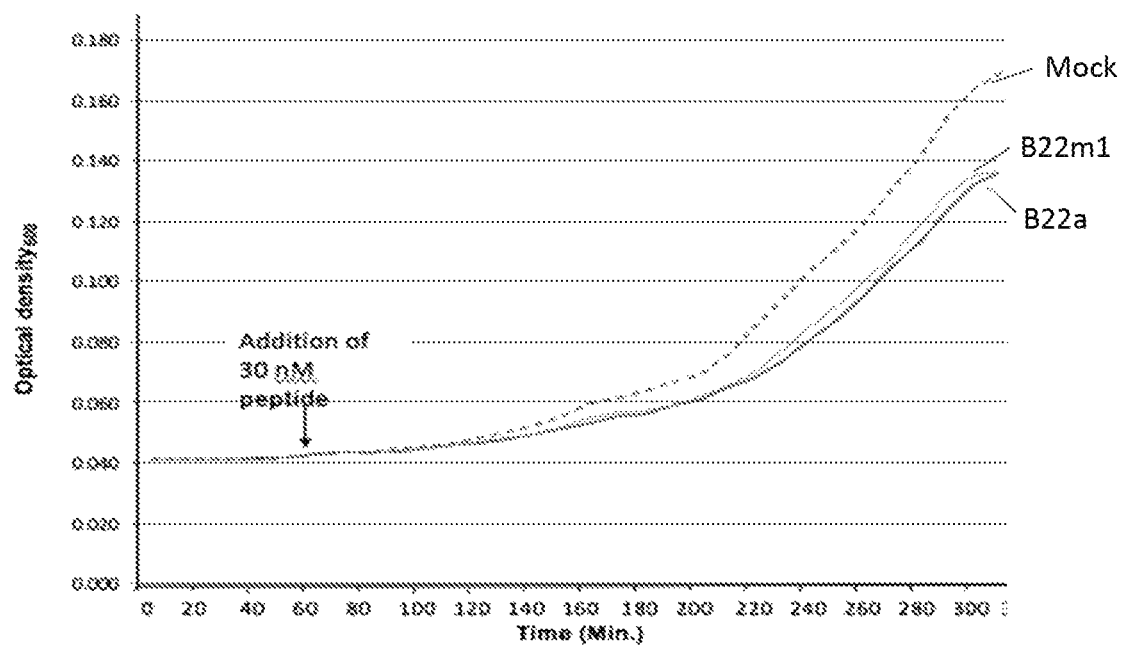
Figure 4:
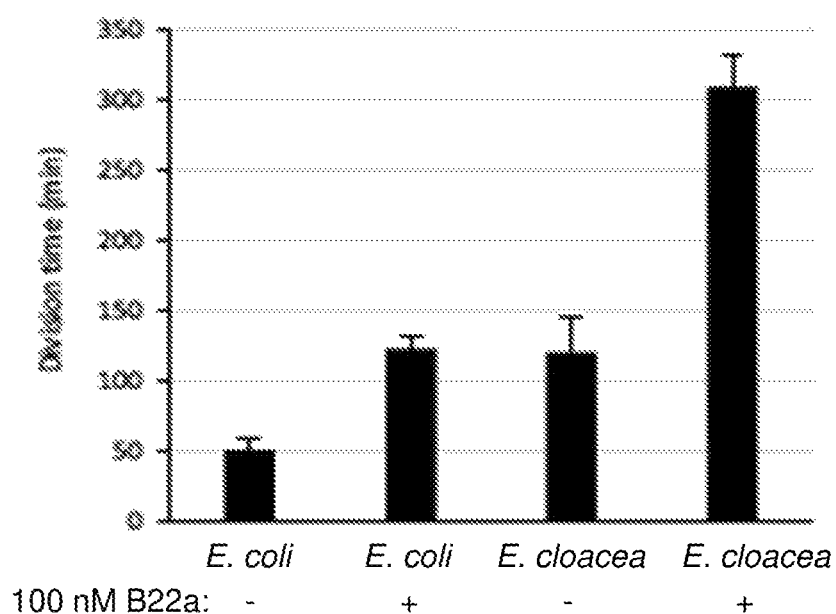

Bacteria growing in biofilms can resist antibiotics due to the formation of extracellular matrix and changes in growth of the bacteria. Several of the bacteria that were killed by either B22 or B22a formed an abundance of extracellular polysaccharides, suggesting that it and similar peptides can penetrate the dense extracellular matrix of bacteria in biofilm. To examine this directly, Enterobacteriacea bacteria were grown into biofilms on a glass surface in a microfluidic chamber and monitored using microscopy. The bacterial cells were stained for 5 min to detect live cells and dead ones at 1 hour intervals. Treatment with either 100 nM of B22 flowed onto the biofilm resulted in rapid death of the bacteria in biofilms (FIGS. 3 and 4). These results show that B22 can kill bacteria growing in biofilms.

The inhibition of biofilm bacteria growth at 100 nM concentrations of the peptides was unexpected. The dogma in the field is that these AMPs are effective at micromolar concentrations where they could intercalate in bacterial membrane, oligomerize, and form a structure in the membrane that enables the influx of water to kill bacteria. The low concentration of B22a that could result in the killing of biofilm bacteria suggests that B22a has an additional activity distinct from the formation of a multi-subunit pore in bacteria.

Example 7: B22a can Kill Bacteria without the Formation of a Multi-Subunit Structure To examine further whether B22a can kill bacteria without the formation of a multi-subunit structure, two additional peptides were chemically synthesized. B22m1 (SEQ ID NO. 5) and B22m2 (SEQ ID NO. 6) both have C-terminal amides. In addition, B22m1 has the phenylalanine at the 9th residue substituted with alanine. B22m2 has two substitutions of the phenylalanines (F) at the 1st and 9th residue with alanines (A). The replacements of the hydrophobic phenylalanines with the smaller and less hydrophobic alanines should reduce the hydrophobic interactions between peptides that will generate a stable oligomer. When tested for bactericidal activity, B22m1 had comparable killing of *E. coli* and *P. aeruginosa* as did B22a. B22m2, with two amino acid substitutions from B22a, had reduced killing, but was still able to reduce viable colony formation by *P. aeruginosa* by more than 2 logs. B22m1 had the same minimal inhibitory concentration for the clinical isolates of *Klebsiella pneumoniae* and for *E. coli* and *P. aeruginosa* as does B22a (Table 3 and Table 4). All of these results support the idea that oligomerization of B22a to form a pore in the bacterial membrane is not required for its bactericidal activity.

TABLE 3

B22a can inhibit the growth of multi-drug resistance clinical isolates of *Klebsiella pneumoniae*.

| K. pneumoniae Strain | MIC (mg/ml) Imipenem | MIC (mg/ml) Meropenem | Colistin | B22a Medium MIC (mM) | B22m1 Medium MIC (mM) |
|---|---|---|---|---|---|
| 88 (NDM1+) | 16 | >16 | NT | 2 | 2 |
| 92 | >64 | >16 | NT | 2 | 2 |
| 109 | 16 | >16 | NT | 2-4 | NT |
| 113 | 16 | >16 | NT | 4 | NT |
| 116 | 8 | >16 | NT | 2-4 | NT |
| 118 | 32 | >16 | NT | 2-4 | NT |
| 136 | 8 | >16 | NT | 4 | NT |
| 170 | NT | >32 | NT | 2 | NT |
| 256 | ≥16 | 4 | NT | 2 | NT |
| 262 (NDM1+) | >16 | ≥6 | >8 | 4 | NT |
| 265 | 48 | ≥64 | NT | 4 | NT |
| 280 | ≥16 | ≥64 | NT | 4 | NT |
| 281 | 4 | >64 | NT | 2-4 | NT |
| 284 | 8 | ≥64 | 16 | 4 | NT |
| 286 | ≥16 | ≥64 | NT | 2 | NT |
| 328 | NT | ≥16 | NT | 4 | NT |
| 330 | 4 | ≥16 | >16 | 4 | NT |
| 361 | >16 | ≥16 | >16 | 8 | NT |
| 365 | NT | ≥16 | NT | 2-4 | NT |
| 399 | NT | ≥16 | NT | 2 | NT |

TABLE 4

Amino acid substitutions in B22m1 did not affect the MIC against *E. coli* and *P. aeruginosa*.

| Name | Sequence | MIC (µM) E. coli ATCC 25922 | MIC (µM) P. aeruginosa PAO1 |
|---|---|---|---|
| B22a | FRKKLKKLFKKLSPVIPLLKLGNH$_2$ | 2 | 2 |
| B22m1 | FRKKLKKLAKKLSPVIPLLKLGNH$_2$ | 2 | 2 |
| B22m2 | ARKKLKKLAKKLSPVIPLLKLGNH$_2$ | 4 | 4 |

To further support the idea that B22a and comparable peptides do not need to form higher order structures to affect bacterial growth, 30 nM of the peptides was added to growing cultures of *P. aeruginosa*. This low concentration of the peptide should further decrease the possibility of peptide oligomerization, as oligomerization should be dependent on the concentration of the peptide. The growth of the bacterial culture was then monitored over time. After the addition of the B22a or B22m1, the growth rate of *P. aeruginosa* was perceptibly reduced (FIGS. 3 and 4). The cell division time of *E. coli* and *Enterobacter cloacae* were also in the absence or presence of 100 nM of B22a. The presence of B22a increased the doubling time of both bacterial by more than 2-fold. These result shows that B22a and B22m1 will decrease bacterial growth. Should B22a and B22m1 inhibit bacteria growth as well as kill bacteria through the formation of higher order structures in the membrane, the peptides may have multiple mechanisms to act against bacteria survival. Peptides that act by multiple mechanisms may result in lower bacterial resistance to the peptides.

Figure 5:
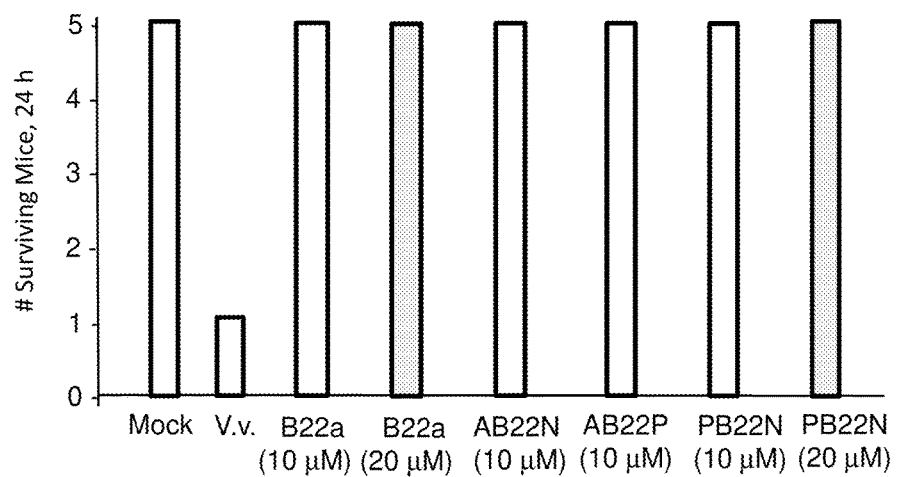

Example 8: B22a can Kill Bacteria without the Formation of a Multi-Subunit Structure Since B22a was effective in preventing infection of *V. vulnificus* in a surgical incision model, we tested it for efficacy for systemic infection in a mouse septicemia model. The B22a was formulated in an isotonic saline solution buffered with phosphates and injected intraperitoneally 1 hour later and morbidity was monitored hourly for two days. Control mice injected with B22a did not exhibit distress or signs of toxicity for during the experiment (FIG. 5). In all of the injected mice, no obvious symptoms were observed. However, at either 10 or 20 µM, B22a did not prevent septicemia.

The lack of efficacy of B22a in inhibiting systemic bacterial infection may have been due to it not being sufficiently stable in vivo. Therefore, three peptides were synthesized that contain the B22 amino acid sequence with additional modifications. Peptide AB22a (SEQ ID NO: 8) has an N-terminal acetyl group ($CH_3C(O)$) and a C-terminal amide ($NH_2$). Peptide AB22P (SEQ ID NO: 9) has an N-terminal acetyl group and a C-terminal polyethyleneglycol (PEG) (PEG=conjugated 8-amino 3,6-dioxaoctanoic acid). Peptide PB22N (SEQ ID NO: 10) has a PEG at both the N-terminus and the C-terminus. In vitro, PB22N was effective in inhibiting the growth of the majority of the Gram-negative bacteria of the Enterobacteriacea. The MICs were approximately two-fold better than that of B22a (Table 5). PB22N was also efficacious in inhibiting antibiotic-resistant clinical isolates of *Klebsiella pneumoniae* (Table 6).

TABLE 5

The MIC of select peptides against twenty representative Gram-negative bacteria of the *Enterobacteriace*.

| | | Minimal inhibitory concentration (µM) | | | | |
|---|---|---|---|---|---|---|
| Species | Strain | LL-37 | BMAP-27B | B22 | B22a | PB22N |
| Enterobacter cloacae | OC4080 | 32 | 4 | 4 | 4 | 0.5 |
| Enterobacter cloacae | OC4092 | >32 | 4 | 4 | 4 | 1 |
| Escherichia coli | ATCC 25922 | 32 | 4 | 2 | 2 | 1 |
| Escherichia coli | ATCC 35218 | 32 | 4 | 4 | 2 | 1 |
| Escherichia coli | IU342 | 32 | 2 | 4 | 2 | 1 |
| Escherichia coli | J53 AzideR | >32 | 4 | 4 | 2 | 1 |
| Escherichia coli | OC4075 | >32 | 4 | 4 | 2 | 1 |
| Escherichia coli | MC4100a | >32 | 4 | 4 | 4 | 1 |
| Escherichia coli | UT189 | >32 | 4 | 2 | 2 | 1 |
| Klebsiella pneumonia | ATCC 700603 | >32 | 4 | 2 | 2 | 1 |
| Klebsiella pneumonia | C2 | >32 | 4 | 4 | 2 | 1 |
| Klebsiella pneumonia | OC4110 | >32 | 8 | 4 | 2 | 1 |
| Klebsiella pneumonia | OC8893 | >32 | 8 | 4 | 2 | 1 |
| Pseudomonas aeruginosa | ATCC 27853 | >32 | 4 | 4 | 2 | 1 |
| Pseudomonas aeruginosa | OC4083 | >32 | 4 | 2 | 2 | 1 |
| Pseudomonas aeruginosa | PAO1 | 32 | 4 | 4 | 2 | 1 |
| Pseudomonas aeruginosa | PAO1 oprD | 32 | 4 | 4 | 2 | 1 |
| Serratia marcescens | 4075A | >32 | >16 | >32 | NT | 32 |
| Serratia marcescens | 4101 | >32 | >16 | >32 | >32 | 32 |
| Serratia marcescens | 4104 | >32 | >16 | >32 | >32 | >32 |

TABLE 6

MIC of B22 and PB22N against drug-resistant clinical isolates of *K. pneumoniae*

| K. pneumoniae Strain | Imipenem | Meropenem | Colistin | B22a (µM) | PB2N (µM) |
|---|---|---|---|---|---|
| 88 (NDM1+) | 16 | >16 | NT | 2 | |
| 92 | >64 | >16 | NT | 2 | |
| 10916 | >16 | | NT | 2-4 | |
| 110113 | 16 | >16 | NT | 4 | |
| 116 | 8 | >16 | NT | 2-4 | 0.5 |
| 118 | 32 | >16 | NT | 2-4 | 0.5 |
| 136 | 8 | >16 | NT | 4 | 0.5 |
| 170 | NT | >32 | NT | 2 | |
| 256 | ≥16 | 4 | NT | 2 | |
| 262 (NDM1+) | >16 | ≥64 | NT | 4 | 2 |
| 265 | 48 | ≥64 | >8 | 4 | |
| 280 | ≥16 | ≥64 | NT | 4 | 2 |
| 281 | 4 | >64 | NT | 2-4 | |
| 284 | 8 | ≥64 | 16 | 4 | |
| 286 | ≥16 | ≥64 | NT | 2 | 2 |
| 328 | NT | ≥16 | NT | 4 | 2 |
| 330 | 4 | ≥16 | >16 | 4 | 0.5 |
| 361 | >16 | ≥16 | >16 | 8 | 8 |
| 365 | NT | ≥16 | NT | 2-4 | |
| 399 | NT | ≥16 | NT | 2 | |

Example 9: The Antimicrobial Peptides can Kill Antibiotic Resistant Bacteria

Carbapenem-resistant *K. pneumoniae* strain 262 was tested for colony formation on nutrient agar after exposure to the minimal inhibitory concentration of B22a. A 45-minute exposure to B22a or PB22N reduced viable colonies by more than 500-fold (Table 7). Thus, the modified B22a and PB22N peptides are not merely inhibitory to bacteria, but are bactericidal.

TABLE 7

B22a and PB22N can rapidly kill antibiotic resistant bacteria.

| | Incubation time (min) | CFU/ml | Fold decr. |
|---|---|---|---|
| *K. pneumoniae* 262 | | | |
| Mock | — | $2.9 \times 10^6$ | 1 |
| B22a | 5 | $<5 \times 10^3$ | 580 |
| B22a | 45 | $<1.2 \times 10^3$ | 2417 |
| PB22N | 5 | $<5 \times 10^3$ | 580 |
| PB22N | 45 | $<2 \times 10^2$ | >2000 |
| *V. cholera* AC53 | | | |
| Mock | — | $1.01 \times 10^6$ | 1 |
| B22a | 45 | $<2 \times 10^3$ | >505 |
| PB22N | 45 | $<8 \times 10^2$ | >1375 |

Bacteria have evolved mechanisms to evade cationic peptides. The pandemic cholera that occurred between 1960 and 1970 had a biotype of *V. cholera* named El-Tor that was resistant to polymyxin B. El-Tor *V. cholera* has acylated lipids and also carrier proteins that can bind and/or export cationic peptides to prevent them from harming the cells. An El-Tor biotype of *V. cholera*, AC53, was sensitive to B22, B22a and PB22N, with an MIC of 2 pM. Furthermore, a 5 min exposure to 2 pM of B22a or PB22N was able to reduce viable colony formation by more than 500-fold, and a 45-minute exposure reduced colony formation by over 2000-fold. These results show that B22a and PB22N were not only able to kill bacteria with modified lipids that conferred resistance to polymyxin but to do so within minutes.

Example 10: B22a can Kill *P. aeruginosa* PAO1 in Biofilm

Figure 6:
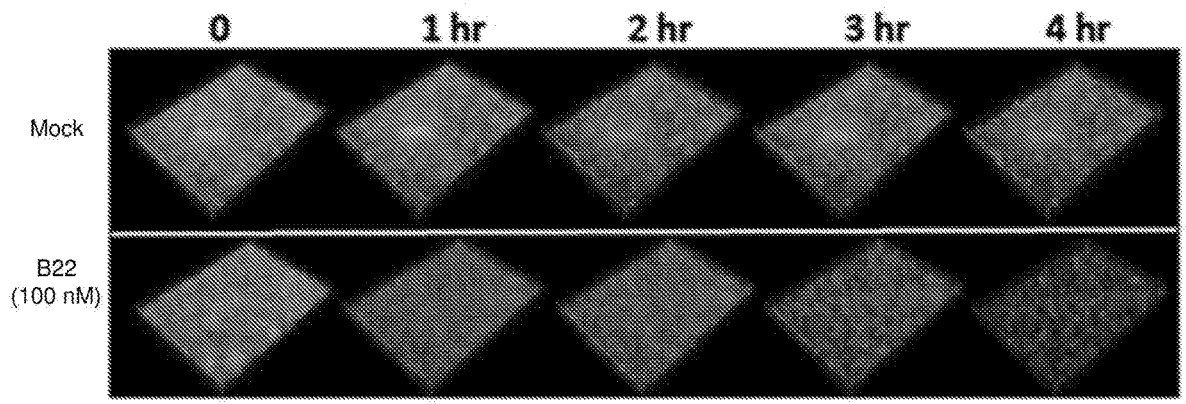
Figure 7:
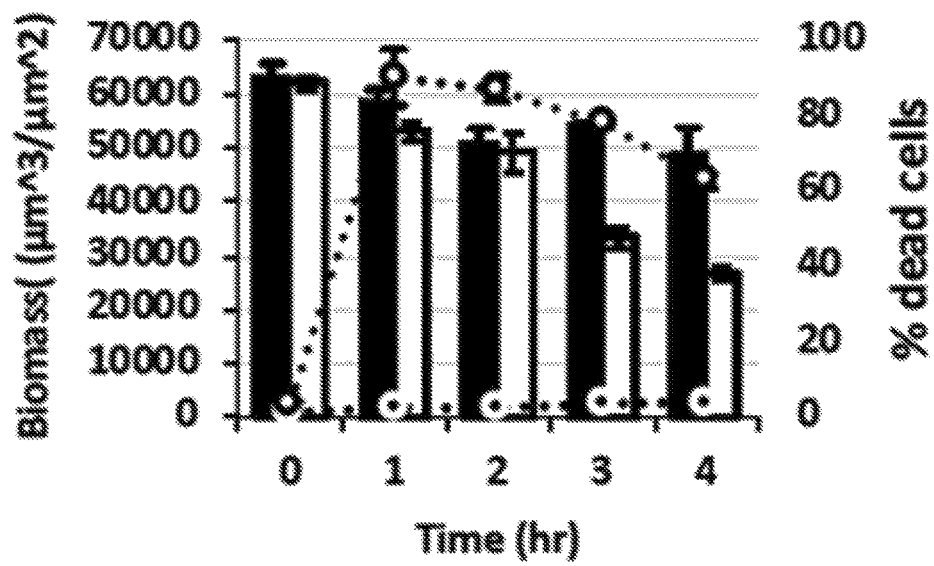
Figure 8:
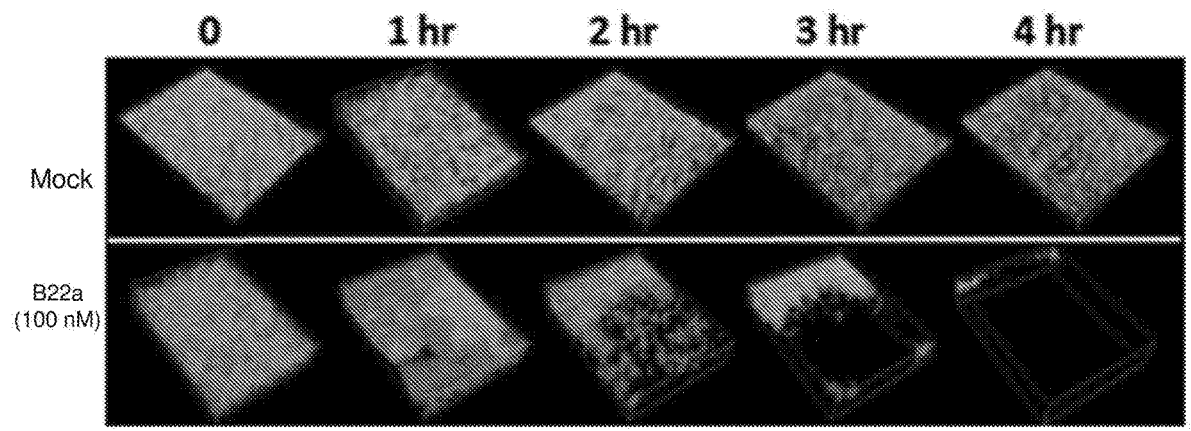
Figure 9:
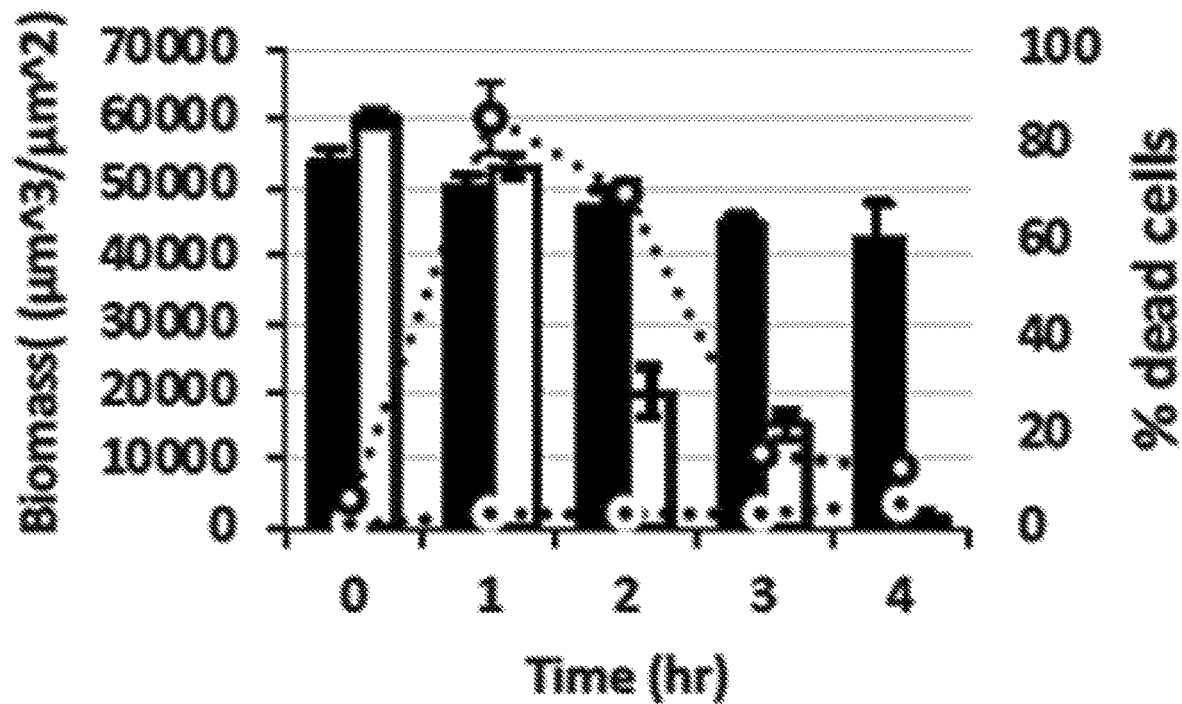

To examine whether B22 and its derivatives can kill bacteria growing in biofilm, *V. cholera* was seeded in a microfluidic chamber and allowed to grow into biofilm. Peptides B22 or B22a were then flowed over the biofilm, and the masses of the viable and nonviable bacteria were quantified by flowing in a stain that differentially stains live and dead bacteria at specified times. Within a 1 hour exposure to either 100 nM of B22 or 100 nM of B22a, an amount of the cells in the biofilm were nonviable as shown in FIG. 6 through FIG. 9. Specifically, FIG. 6 shows two level of fluorescent cell images, with the top row displaying the mock-treatment and the bottom row displaying the treatment with B22. The top shows the change in the cell viability over time. The second row shows that treatment with 100 nM of B22 caused the cells to die and cell death increased over time without the addition of more B22. FIG. 7 shows a graph quantifying the total biomass of *V. cholera* mock-treated (black bars) and treated (white bars) with B22, and the percentage of dead cells within the biofilms (untreated and, black circles; and treated, white circles). FIG. 8 shows two level of fluorescent cell images, with the top row displaying the mock-treatment and the bottom row displaying the treatment with B22a. The top shows the change in the cell viability over time. The second row shows that treatment with 100 nM of B22a caused the cells to die and cell death increased over time without the addition of more B22a. FIG. 9 shows a graph quantifying the total biomass of *V. cholera* mock-treated (black bars) and treated (white bars) with B22a, and the percentage of dead cells within the biofilms (untreated and, black circles; and treated, white circles). The amounts of nonviable cells also increased with the time of treatment. In fact, some of the cells were so disrupted, they no longer picked up the dye that enters dead bacteria. Similar results were observed with biofilm formed by *P. aeruginosa* PAO1. These results show that B22 and B22a could penetrate the extracellular matrix of biofilm bacteria and kill them.

Figure 10:
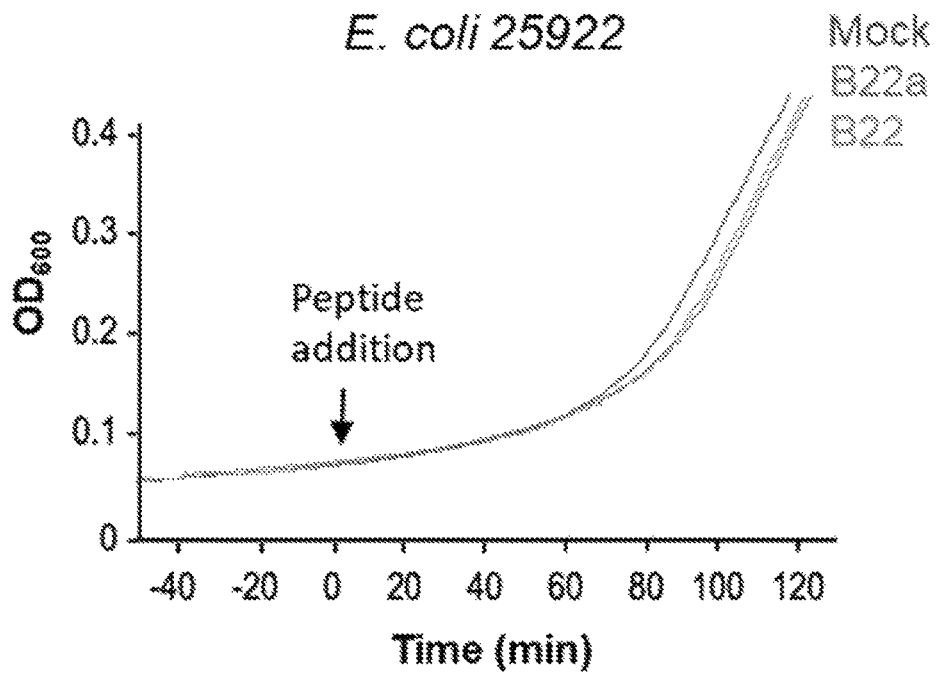
Figure 11:
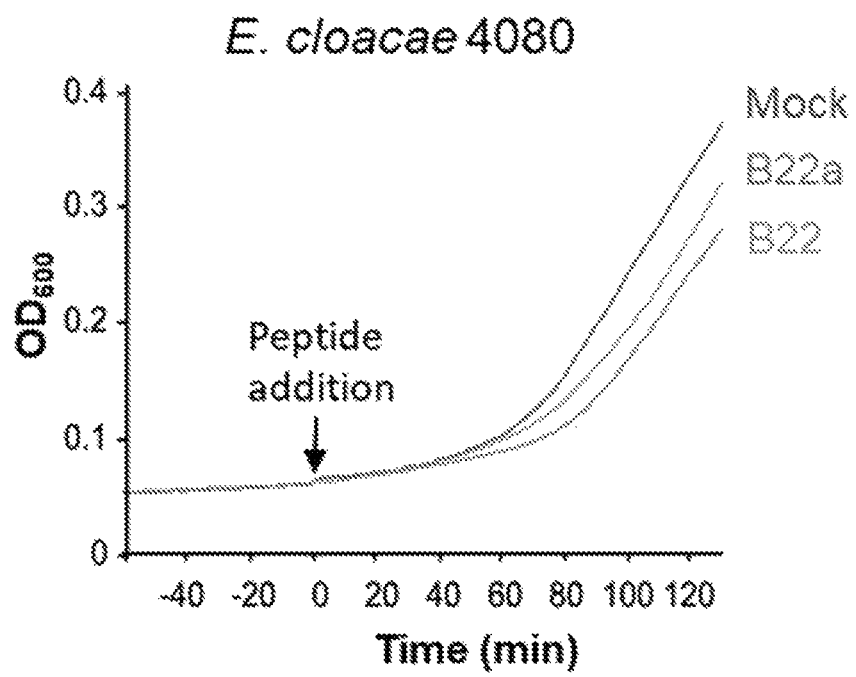

Example 11: B22a can Inhibit Growth of Gram-Negative Bacteria at Sub-Lethal Concentrations In treating bacterial infection, the antibiotic needs to be dosed to accumulate at a critical concentration and be maintained for a time period sufficient to kill the target bacteria. The effective concentration will be especially important for cathelicidins because bactericidal activity requires that the peptides bind to lipids and oligomerize to disrupt the bacterial membrane (Kao et al., 2016; Wang, 2008). We wondered if a sub-lethal concentration of B22 and B22a would have any discernable effects on bacteria. In the colony formation assays, nanomolar concentrations of the peptides did not noticeably reduce the number of colonies formed. However, some of the colonies appeared to have slightly reduced diameters compared to mock-treated bacteria, suggesting that sub-lethal concentrations of the peptides could affect the growth rate of bacteria. To assess this quantitatively, cultures of growing *E. coli* and *E. cloacae* were adjusted to contain 30 nM of B22 or B22a, and the culture densities were monitored over time. Interestingly, both *E. coli* and *E. cloacae* had reduced growth rates after treatment with 30 nM concentrations of the peptides as shown in FIG. 10 and FIG. 11. *P. aeruginosa*, *V. cholera* and other Gram-negative bacteria were also observed to have reduced growth rates with sub-lethal concentrations of B22 or B22a.

Figure 12:
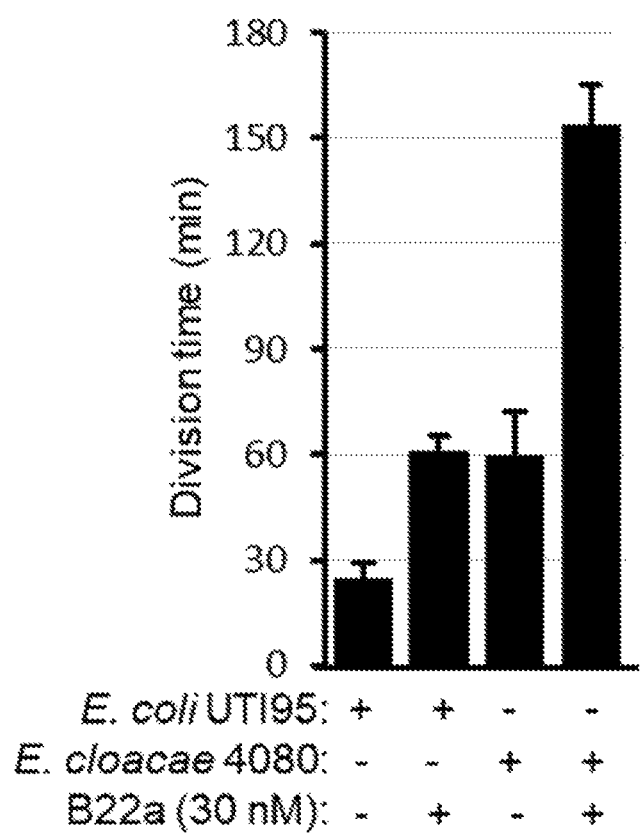

To confirm that sub-lethal concentrations of peptide are reducing bacterial growth, the time required for division of individual bacterial cells in the presence of B22a was monitored. The division times for a clinical isolate of *E. coli*, UTI95 and *E. cloacae* 4080 were increased by about 2-fold in the presence of 30 nM of B22a as shown in FIG. 12. Specifically, FIG. 12 shows that B22a can increase cell division time, consistent with a reduction in the growth rate, and wherein *E. coli* and *E. cloacae* were incubated without or with 30 nM B22a and cell division time was recorded by time-lapse phase contrast microscopy. These results show that B22 and B22a could affect bacterial growth when administered at levels lower than needed for bactericidal activity.

Figure 13:
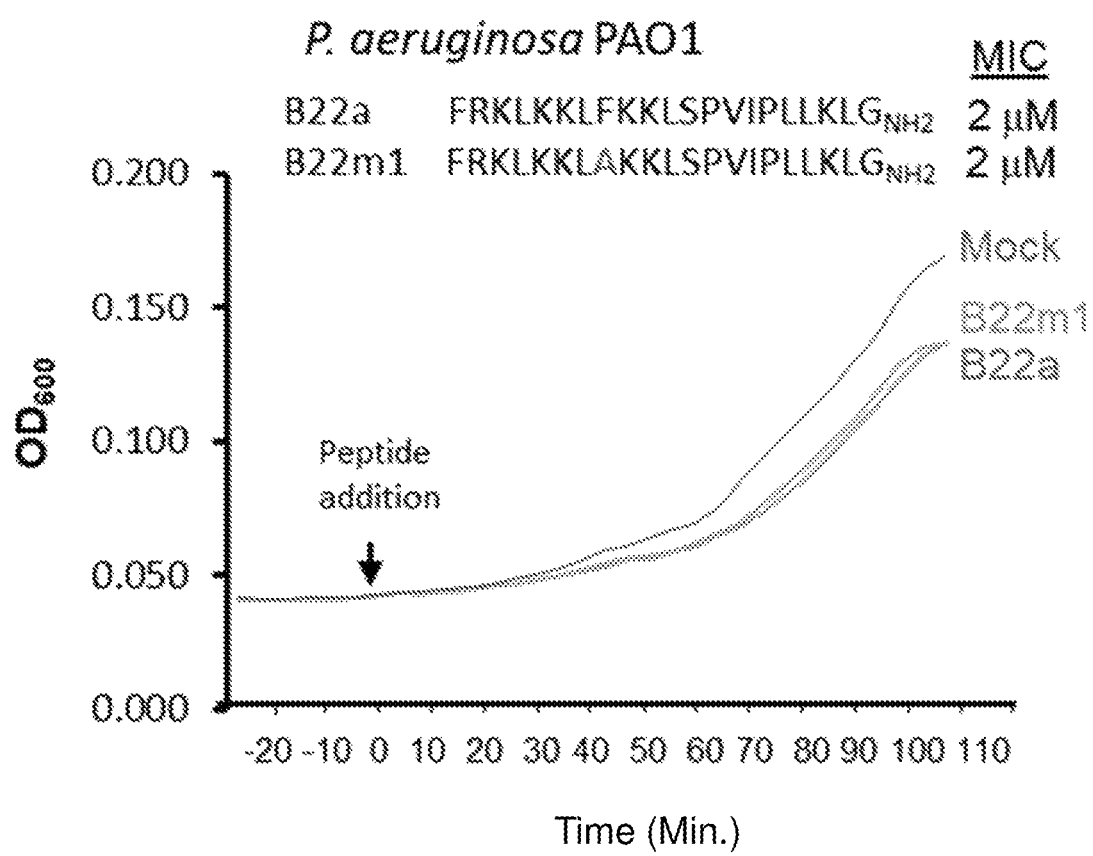

Example 12: B22m1 can Inhibit *P. aeruginosa* PAO1 Growth Independent of Oligomerization Forming pores in the bacterial membrane will require sufficient concentrations of peptides that assemble into structures to breach the membrane. Lower concentration of the peptides will decrease the rate of oligomerization when compared to higher concentrations. Given that B22 and B22a could affect bacterial growth at 20-30 nM, it is possible that oligimerization is not required for affecting bacterial growth. To test this hypothesis, amino acid substitutions in B22 were made and tested. B22 is modeled to be an amphipathic helix in its N-terminal region. Phenylalanine 8 in B22 is predicted to be in the hydrophobic surface in the amphipathic helix that can contact the hydrophobic surface of another B22 molecule. We synthesized a peptide named B22m1 that substitutes phenylalanine 8 with an alanine and tested it at 30 nM concentration. B22m1 which also contains a C-terminal amide, reduced the growth of *P. aeruginosa* PAO1 to a level comparable to that of B22a as shown in FIG. 13. Specifically, FIG. 13 shows the growth rate of *P. aeruginosa* PAO1 was reduced by both 30 nM of B22a and B22m1. The MIC of B22m1 and B22a, respectively, against *P. aeruginosa* PAO1 was 2 pM. These results suggest that B22a could affect Gram-negative bacterial growth in a manner independent of the oligomerization of B22a. Given that higher concentrations of B22a forms pores in bacterial membrane, B22a has a second activity to inhibit bacterial growth. This suggests that bacteria are less likely to become resistant to inhibitors with multiple activities.

---

What is claimed is:

1. An antimicrobial peptide comprising the amino acid sequence of $$X_6RKKX_7KKLX_8KKLSPVIPLLX_9X_{10}X_{11}$$ (SEQ ID NO: 3)

wherein $X_6$ is F, L or A, $X_8$ 7 is F or L, $X_8$ is F or A, $X_9$ is H or K, $X_{10}$ is L, $X_{11}$ is G, and $X_{11}$ is optionally C-terminally amidated, provided that when $X_7$ is F, $X_6$ is L; or a pharmaceutically salt thereof.

2. The antimicrobial peptide of claim 1, wherein $X_9$ is K; or a pharmaceutically acceptable salt thereof.

3. The antimicrobial peptide of claim 1, wherein $X_7$ is L; or a pharmaceutically acceptable salt thereof.

4. The antimicrobial peptide of claim 1, wherein the antimicrobial peptide is C-terminally amidated.

5. The antimicrobial peptide of claim 1, wherein the antimicrobial peptide comprises a sequence that is selected from the group consisting of SEQ ID NO:4, SEQ ID NO:5, SEQ ID NO:6, and SEQ ID NO: 8, or a pharmaceutically acceptable salt thereof.

6. The antimicrobial peptide of claim 1, wherein the antimicrobial peptide comprises a sequence that is at least 95% identical to a sequence selected from the group consisting of SEQ ID NO: 4, SEQ ID NO: 5, and SEQ ID NO: 6; or a pharmaceutically acceptable salt thereof.

7. The antimicrobial peptide of claim 1, wherein the antimicrobial peptide comprises a sequence that is at least 95% identical SEQ ID NO: 8 or a pharmaceutically acceptable salt thereof.

8. The antimicrobial peptide of claim 1, wherein the antimicrobial peptide comprises SEQ ID NO: 4; or a pharmaceutically acceptable salt thereof.

9. The antimicrobial peptide of claim 1, wherein the antimicrobial peptide comprises SEQ ID NO: 5; or a pharmaceutically acceptable salt thereof.

10. The antimicrobial peptide of claim 1, wherein the antimicrobial peptide comprises SEQ ID NO: 6; or a pharmaceutically acceptable salt thereof.

11. The antimicrobial peptide of claim 1, wherein the antimicrobial peptide comprises SEQ ID NO: 8; or a pharmaceutically acceptable salt thereof.

* * * * *